US006090597A

United States Patent [19]
Hirano et al.

[11] Patent Number: 6,090,597
[45] Date of Patent: *Jul. 18, 2000

[54] METHOD OF PRODUCING L-LYSINE

[75] Inventors: Seiko Hirano; Masakazu Sugimoto; Eiichi Nakano; Masako Izui; Atsushi Hayakawa; Yasuhiko Yoshihara; Tsuyoshi Nakamatsu, all of Kawasaki, Japan

[73] Assignee: Ajinomoto Co., Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/852,730

[22] Filed: May 7, 1997

[30] Foreign Application Priority Data

Jun. 5, 1996 [JP] Japan .................................. 8-142812

[51] Int. Cl.⁷ .............................. C12P 13/08; C12N 1/20; C12N 15/00; C07H 21/04
[52] U.S. Cl. .......................... 435/115; 435/189; 435/197; 435/252.3; 435/320.1; 536/23.2
[58] Field of Search ................................... 435/115, 189, 435/197, 252.32, 252.3, 320.1; 536/23.2

[56] References Cited

U.S. PATENT DOCUMENTS

| | | | |
|---|---|---|---|
| 4,861,722 | 8/1989 | Sano et al. | 435/252.32 |
| 4,980,285 | 12/1990 | Sano et al. | 435/108 |
| 5,426,052 | 6/1995 | Flickinger et al. | 536/23.2 |

FOREIGN PATENT DOCUMENTS

| | | |
|---|---|---|
| 0 435 132 | 7/1991 | European Pat. Off. . |
| 05284970 | 11/1993 | Japan . |
| WO 95/16042 | 6/1995 | WIPO . |
| WO 96/40934 | 12/1996 | WIPO . |

OTHER PUBLICATIONS

Patent Abstracts of Japan, vol. 18, No. 71, (C–1162), Feb. 7, 1994, JP–5–284970, Nov. 2, 1993.
Patent Abstracts of Japan, vol. 95, No. 6, Jul. 31, 1995, JP–7–075579, Mar. 20, 1995.
Patent Abstracts of Japan, vol. 11, No. 159, (C–423), May 22, 1987, JP–61–289887, Dec. 19, 1986.
Schrumpf et al. (1991) A functionally split pathway for lysine synthesis in *Corynebacterium glutamicum.* J. Bacteriology 173 (14): 4510–4516, Jan. 1991.
Sonntag et al. (1993) Flux partitioning in the split pathway of lysine synthesis in *Corynebacterium glutamicum.* Quantification by carbon–13 and proton NMR spectroscopy. European Journal of Biochemistry 213 (3): 1325–1331, Jan. 1993.
S. Bonnassie et al, "Nucleotide sequence of the dapA gene from *Cornyebacterium glutamicum*", Oxford University Press, Nucleic Acids Research, vol. 18, No. 21, pp. 6421, Oct. 3, 1990.
A. Pisabarro et al, "A cluster of three genes (dapA, orf2, and dapB) of *Brevilbacterium lactofermentum* encodes dihydrokipicolinate synthase, dihydrodipicolinate reductase, and a third polypeptide of unknown function", Journal of Bacteriology, vol. 175, No. 9, pp. 2743–2749, May 1993.

*Primary Examiner*—Bradley Sisson
*Assistant Examiner*—Einar Stole
*Attorney, Agent, or Firm*—Oblon, Spivak, McClelland, Maier & Neustadt, P.C.

[57] ABSTRACT

A coryneform bacterium in which a DNA coding for a diaminopimelate decarboxylase and a DNA coding for a diaminopimelate dehydrogenase are enhanced is cultivated in a medium to allow L-lysine to be produced and accumulated in a culture, and L-lysine is collected from the culture.

8 Claims, 14 Drawing Sheets

METHOD OF PRODUCING L-LYSINE

BACKGROUND OF THE INVENTION

The present invention relates to a method for producing L-lysine by cultivating a microorganism obtained by modifying a coryneform bacterium used for fermentative production of amino acids or the like by means of a technique based on genetic engineering.

L-Lysine, which is used as a fodder additive, is usually produced by a fermentative method by using an L-lysine-producing mutant strain belonging to the coryneform bacteria. Various L-lysine-producing bacteria known at present are those created by artificial mutation starting from wild type strains belonging to the coryneform bacteria.

As for the coryneform bacteria, there are disclosed a vector plasmid which is autonomously replicable in bacterial cells and has a drug resistance marker gene (see U.S. Pat. No. 4,514,502), and a method for introducing a gene into bacterial cells (for example, Japanese Patent Application Laid-open No. 2-207791). There is also disclosed a possibility for breeding an L-threonine- or L-isoleucine-producing bacterium by using the techniques as described above (see U.S. Pat. Nos. 4,452,890 and 4,442,208). As for breeding of an L-lysine-producing bacterium, a technique is known, in which a gene participating in L-lysine biosynthesis is incorporated into a vector plasmid to amplify the gene in bacterial cells (for example, Japanese Patent Application Laid-open No. 56-160997).

Known genes for L-lysine biosynthesis include, for example, a dihydrodipicolinate reductase gene (Japanese Patent Application Laid-open No. 7-75578) and a diaminopimelate dehydrogenase gene (Ishino, S. et al., *Nucleic Acids Res.*, 15, 3917 (1987)), which are cloned genes which participate in L-lysine biosynthesis, as well as a phosphoenolpyruvate carboxylase gene (Japanese Patent Application Laid-open No. 60-87788), a dihydrodipicolinate synthase gene (Japanese Patent Publication No. 6-55149), and a diaminopimelate decarboxylase gene (Japanese Patent Application Laid-open No. 60-62994), amplification of which affects L-lysine productivity.

As described above, certain successful results to improve L-lysine productivity have been obtained by means of amplification of genes for the L-lysine biosynthesis. However, amplification of some genes decreases growth speed of bacteria although the amplification improves L-lysine productivity, resulting in decrease of rate of L-lysine production.

No case has been reported in which growth is intended to be improved by enhancing a gene for L-lysine biosynthesis as well. In the present circumstances, no case is known for the coryneform bacteria, in which anyone has succeeded in remarkable improvement in L-lysine yield without restraining growth, by combining a plurality of genes for L-lysine biosynthesis.

SUMMARY OF THE INVENTION

An object of the present invention is to improve the L-lysine-producing ability without decreasing the growth speed of a coryneform bacterium, by enhancing a plurality of genes for L-lysine biosynthesis in combination in the coryneform bacteria.

When an objective substance is produced fermentatively by using a microorganism, the production speed, as well as the yield of the objective substance relative to an introduced material, is an extremely important factor. An objective substance may be produced remarkably inexpensively by increasing the production speed per a unit of fermentation equipment. Accordingly, it is industrially extremely important that the fermentative yield and the production speed are compatible with each other. The present invention proposes a solution for the problem as described above in order to fermentatively produce L-lysine by using a coryneform bacterium.

The principle of the present invention is based on the fact that the growth of a coryneform bacterium can be improved, and the L-lysine-producing speed thereof can be improved by enhancing both of a DNA sequence coding for a diaminopimelate dehydrogenase (a diaminopimelate dehydrogenase is hereinafter referred to as "DDC", and a gene coding for a DDC protein is hereinafter referred to as "lysA", if necessary), and a DNA sequence coding for a diaminopimelate decarboxylase (a diaminopimelate decarboxylase is hereinafter referred to as "DDH", and a gene coding for a DDH protein is hereinafter referred to as "ddh", if necessary) compared with the case in which these DNA sequences are each enhanced singly.

Namely, the present invention lies in a recombinant DNA autonomously replicable in cells of coryneform bacteria, comprising a DNA sequence coding for a diaminopimelate dehydrogenase and a DNA sequence coding for a diaminopimelate decarboxylase.

In another aspect, the present invention provides a coryneform bacterium harboring an enhanced DNA sequence coding for a diaminopimelate dehydrogenase and an enhanced DNA sequence coding for a diaminopimelate decarboxylase.

In still another aspect, the present invention provides a method for producing L-lysine comprising the steps of cultivating the coryneform bacterium described above in a medium to allow L-lysine to be produced and accumulated in a culture, and collecting L-lysine from the culture.

The coryneform bacteria referred to in the present invention are a group of microorganisms as defined in *Beraey's Manual of Determinative Bacteriology*, 8th ed., p. 599 (1974), which are aerobic Gram-positive non-acid-fast rods having no spore-forming ability. The coryneform bacteria include bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium.

According to the present invention, the L-lysine-producing ability of coryneform bacteria can be improved, and the growth speed can be also improved. The present invention can be applied to ordinary L-lysine-producing bacteria as well as strains with high L-lysine productivity.

DETAILED DESCRIPTION OF THE INVENTION

Figure 1:
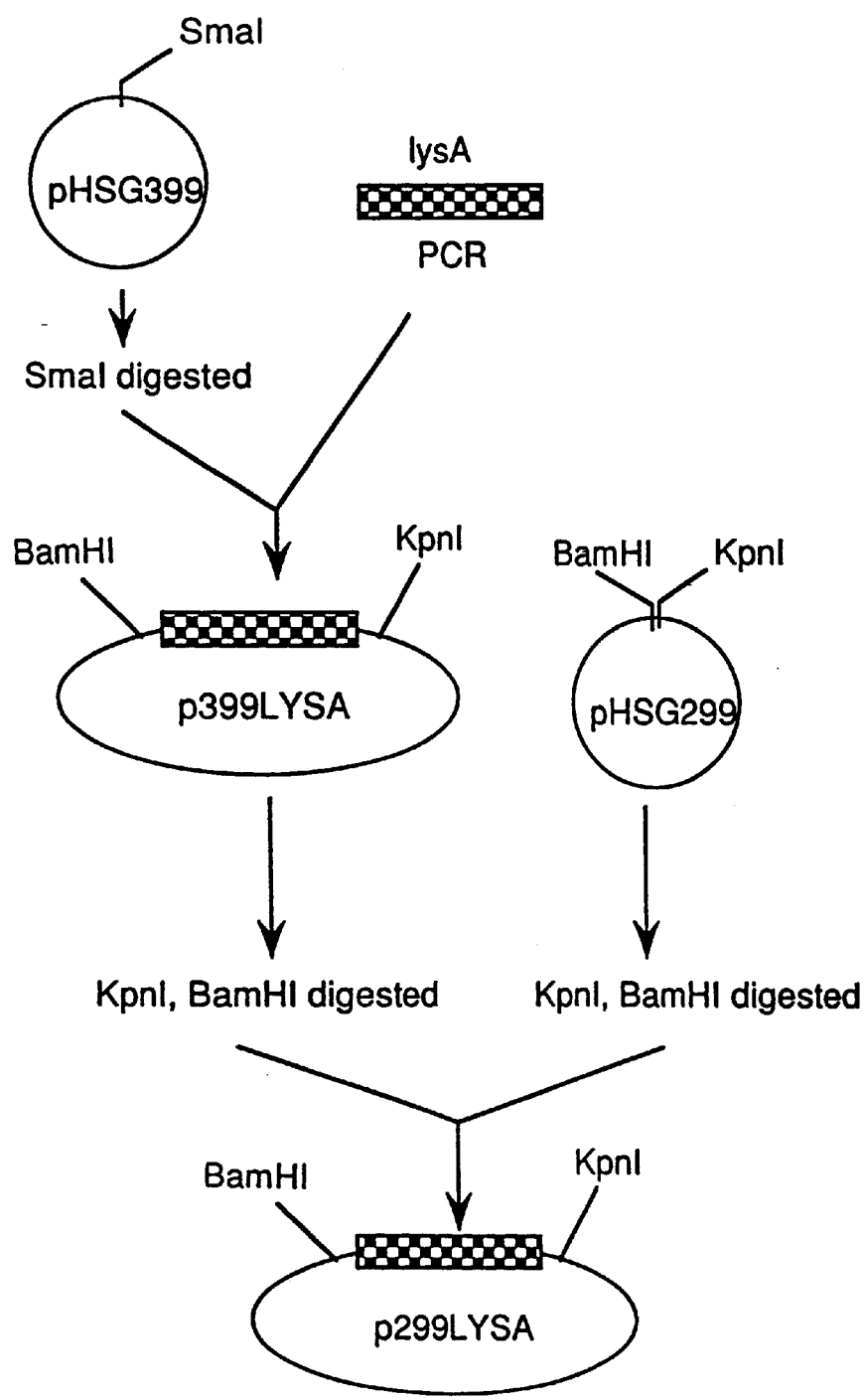
FIG. 1 illustrates a process of construction of a plasmid p299LYSA carrying lysA.

The present invention will be explained in detail below.
<1> Preparation of genes for L-lysine biosynthesis used for the present invention The genes for L-lysine biosynthesis used in the present invention can be obtained respectively by preparing chromosomal DNA from a bacterium as a DNA donor, constructing a chromosomal DNA library by using a plasmid vector or the like, selecting a strain harboring a desired gene from the library, and recovering, from the selected strain, recombinant DNA into which the gene has been inserted. The DNA donor for the gene for L-lysine biosynthesis used in the present invention is not specifically limited provided that the desired gene for L-lysine biosynthesis expresses an enzyme protein which functions in cells of coryneform bacteria. However, the DNA donor is preferably a coryneform bacterium.

Both of the genes of lysA and ddh originating from coryneform bacteria have known sequences. Accordingly, they can be obtained by performing amplification in accordance with the polymerase chain reaction method (PCR; see White, T. J. et al., *Trends Genet.*, 5, 185 (1989)).

Each of the genes for L-lysine biosynthesis used in the present invention is obtainable in accordance with certain methods as exemplified below.

(1) Preparation of mutant lysA lysA can be isolated from chromosome of a coryneform bacterium by preparing chromosomal DNA in accordance with, for example, a method of Saito and Miura (H. Saito and K. Miura, *Biochem. Biophys. Acta*, 72, 619 (1963)), and amplifying lysA in accordance with the polymerase chain reaction method (PCR; see White, T. J. et al., *Trends Genet.*, 5, 185 (1989)). The DNA donor is not specifically limited, however, it is exemplified by *Brevibacterium lactofermentum* ATCC 13869 strain.

In the coryneform bacteria, lysA forms an operon together with argS (arginyl-tRNA synthase gene), and lysA exists downstream from argS. Expression of lysA is regulated by a promoter existing upstream from argS (see *Journal of Bacterioloav, Nov.*, 7356–7362 (1993)). DNA sequences of these genes are known for *Corynebacterium glutamicum* (see *Molecular Microbiology*, 4(11), 1819–1830 (1990); *Molecular and General Genetics*, 212, 112–119 (1988)), on the basis of which DNA primers for PCR can be prepared. Such DNA primers are specifically exemplified by DNA's of 23-mers respectively having nucleotide sequences shown in SEQ ID NO: 1 in Sequence Listing (corresponding to nucleotide numbers 11 to 33 in a nucleotide sequence described in *Molecular Microbiology*, 4(11), 1819–1830 (1990)) and SEQ ID NO: 2 (corresponding to nucleotide numbers 1370 to 1392 in a nucleotide sequence described in *Molecular and General Genetics*, 212, 112–119 (1988)).

In Example described later on, a DNA fragment containing a promoter, argS, and lysA was used in order to enhance lysA. However, argS is not essential for the present invention. It is allowable to use a DNA fragment in which lysA is ligated just downstream from a promoter.

A nucleotide sequence of a DNA fragment containing argS and lysA, and an amino acid sequence deduced to be encoded by the nucleotide sequence are exemplified in SEQ ID NO: 3. An example of an amino acid sequence encoded by argS is shown in SEQ ID NO: 4, and an example of an amino acid sequence encoded by lysA is shown in SEQ ID NO: 5. In addition to DNA fragments coding for these amino acid sequences, the present invention can equivalently use DNA fragments coding for amino acid sequences substantially the same as the amino acid sequence shown in SEQ ID NO: 5, namely amino acid sequences having mutation based on, for example, substitution, deletion, or insertion of one or more amino acids provided that there is no substantial influence on the DDC activity.

DNA can be synthesized in accordance with an ordinary method by using DNA synthesizer model 380B produced by Applied Biosystems and using the phosphoamidite method (see *Tetrahedron Letters* (1981), 22, 1859). PCR can be performed by using DNA Thermal Cycler Model PJ2000 produced by Takara Shuzo, and using Taq DNA polymerase in accordance with a method designated by the supplier.

It is preferred that lysA amplified by PCR is ligated with vector DNA autonomously replicable in cells of *E. coli* and/or coryneform bacteria to prepare recombinant DNA, and the recombinant DNA is introduced into cells of *E. coli* beforehand. Such provision makes following operations easy. The vector autonomously replicable in cells of *E. coli* is preferably a plasmid vector which is preferably autonomously replicable in cells of a host, including, for example, pUC19, pUC18, pBR322, pHSG299, pHSG399, pHSG398, and RSF1010.

When a DNA fragment having an ability to allow a plasmid to be autonomously replicable in coryneform bacteria is inserted into these vectors, they can be used as a so-called shuttle vector autonomously replicable in both *E. coli* and coryneform bacteria.

Such a shuttle vector includes the followings. Microorganisms harboring each of vectors and accession numbers in international depositary authorities are shown in parentheses.

pHC4: *Escherichia coli* AJ12617 (FERM BP-3532)
pAJ655: *Escherichia coli* AJ11882 (FERM BP-136)
  *Corynebacterium glutamicum* SR8201 (ATCC 39135)
pAJ1844: *Escherichia coli* AJ11883 (FERM BP-137)
  *Corynebacterium glutamicum* SR8202 (ATCC 39136)
pAJ611: *Escherichia coli* AJ11884 (FERM BP-138)
pAJ3148: *Corynebacterium glutamicum* SR8203 (ATCC 39137)
pAJ440: *Bacillus subtilis* AJ11901 (FERM BP-140)

These vectors are obtainable from the deposited microorganisms as follows. Cells collected at a logarithmic growth phase were lysed by using lysozyme and SDS, followed by separation from a lysate by centrifugation at 30,000×g to obtain a supernatant. Polyethylene glycol is added to the supernatant, followed by fractionation and purification by means of cesium chloride-ethidium bromide equilibrium density gradient centrifugation.

E. coli can be transformed by introducing a plasmid in accordance with, for example, a method of D. M. Morrison (Methods in Enzymology, 68, 326 (1979)) or a method in which recipient cells are treated with calcium chloride to increase permeability for DNA (Mandel, M. and Higa, A., J. Mol. Biol., 53, 159 (1970)).

(2) Preparation of ddh

A DNA fragment containing ddh can be prepared from chromosome of a coryneform bacterium by means of PCR. The DNA donor is not specifically limited, however, it is exemplified by Brevibacterium lactofermentum ATCC 13869 strain.

A DDH gene is known for Corynebacterium glutamicum (Ishino, S. et al., Nucleic Acids Res., 15, 3917 (1987)), on the basis of which primers for PCR can be prepared. Such DNA primers are specifically exemplified by DNA's of 20-mers respectively having nucleotide sequences shown in SEQ ID NOs: 6 and 7 in Sequence Listing. Synthesis of DNA, PCR, and preparation of a plasmid carrying obtained ddh can be performed in the same manner as those for lysA described above.

A nucleotide sequence of a DNA fragment containing ddh and an amino acid sequence deduced from the nucleotide sequence are illustrated in SEQ ID NO: 8. Only the amino acid sequence is shown in SEQ ID NO: 9. In addition to DNA fragments coding for this amino acid sequence, the present invention can equivalently use DNA fragments coding for amino acid sequences substantially the same as the amino acid sequence shown in SEQ ID NO: 9, namely amino acid sequences having mutation based on, for example, substitution, deletion, or insertion of one or more amino acids provided that there is no substantial influence on the DDH activity.

<2> Recombinant DNA and coryneform bacterium of the present invention

The coryneform bacterium of the present invention harbors a DNA sequence coding for diaminopimelate decarboxylase (lysA) and a DNA sequence coding for diaminopimelate dehydrogenase (ddh) which are enhanced. The term "a DNA sequence is enhanced" herein refers to the fact that the intercellular activity of an enzyme encoded by the DNA sequence is raised by, for example, increasing the copy number of a gene, using a strong promoter, using a gene coding for an enzyme having a high specific activity, or combining these means.

The coryneform bacterium to which the DNA sequences described above is an L-lysine-producing coryneform bacterium, examples of which include L-lysine-producing wild type strains and artificial mutant strains and coryneform bacteria enhanced in L-lysine productivity by genetic engineering. Even if the bacterium has low L-lysine productivity, the L-lysine productivity can be improved by enhancing lysA and ddh. If the bacterium has high L-lysine productivity, the L-lysine production efficiency can be more raised by enhancing lysA and ddh.

(1) L-Lysine-producing strain belonging to coryneform bacteria

Examples of the coryneform bacterium used to introduce lysA and ddh include, for example, the following lysine-producing strains:

Corynebacterium acetoacidophilum ATCC 13870;
Corynebacterium acetoglutamicum ATCC 15806;
Corynebacterium callunae ATCC 15991;
Corynebacterium glutamicum ATCC 13032;
(Brevibacterium divaricatum) ATCC 14020;
(Brevibacterium lactofermentum) ATCC 13869;
(Corynebacterium lilium) ATCC 15990;
(Brevibacterium flavum) ATCC 14067;
Corynebacterium melassecola ATCC 17965;
Brevibacterium saccharolyticum ATCC 14066;
Brevibacterium immariophilum ATCC 14068;
Brevibacterium roseum ATCC 13825;
Brevibacterium thiogenitalis ATCC 19240;
Microbacterium ammoniaphilum ATCC 15354;
Corynebacterium thermoaminogenes AJ12340 (FERM BP-1539).

Other than the bacterial strains described above, those usable as a host in which lysA and ddh are to be enhanced include, for example, mutant strains having an L-lysine-producing ability derived from the aforementioned strains. Such artificial mutant strains include the followings: S-(2-aminoethyl)-cysteine (hereinafter abbreviated as "AEC") resistant mutant strains (Brevibacterium lactofermentum AJ11082 (NRRL B-11470), Japanese Patent Publication Nos. 56-1914, 56-1915, 57-14157, 57-14158, 57-30474, 58-10075, 59-4993, 61-35840, 62-24074, 62-36673, 5-11958, 7-112437, and 7-112438); mutant strains which require an amino acid such as L-homoserine for their growth (Japanese Patent Publication Nos. 48-28078 and 56-6499); mutant strains which exhibit resistance to AEC and require amino acids such as L-leucine, L-homoserine, L-proline, L-serine, L-arginine, L-alanine, and L-valine (U.S. Pat. Nos. 3,708,395 and 3,825,472); L-lysine-producing mutant strains which exhibit resistance to DL-α-amino-ε-caprolactam, α-amino-lauryllactam, aspartate-analog, sulfa drug, quinoid, and N-lauroylleucine; L-lysine-producing mutant strains which exhibit resistance to inhibitors of oxyaloacetate decarboxylase or respiratory system enzymes (Japanese Patent Application Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); L-lysine-producing mutant strains which require inositol or acetic acid (Japanese Patent Application Laid-open Nos. 55-9784 and 56-8692); L-lysine-producing mutant strains which exhibit sensitivity to fluoropyruvic acid or temperature not less than 34° C. (Japanese Patent Application Laid-open Nos. 55-9783 and 53-86090); and production mutant strains belonging to the genus Brevibacterium or Corynebacterium which exhibit resistance to ethylene glycol and produce L-lysine (U.S. Pat. No. 4,411,997).

(2) L-Lysine-producing coryneform bacteria having L-lysine productivity enhanced by genetic recombination The L-lysine producing speed can be further improved by enhancing lysA and ddh, if the coryneform bacterium has been enhanced in L-lysine production by genetic engineering, for example, by introducing a gene coding for an enzyme having a mutation which causes desensitization in feedback inhibition, wild type of which enzyme is subjected to feedback inhibition among enzymes participating in L-lysine biosynthesis, or by enhancing a gene for L-lysine biosynthesis other than lysA and ddh.

The coryneform bacterium enhanced in L-lysine productivity includes a coryneform bacterium harboring a DNA sequence coding for an aspartokinase which is desensitized in feedback inhibition by L-lysine and L-threonine (an aspartokinase is hereinafter referred to as "AK", a gene coding for an AK protein is hereinafter referred to as "lysC", and a gene coding for an AK protein which is desensitized in feedback inhibition by L-lysine and L-threonine, if necessary), and an enhanced DNA sequence coding for a dihydrodipicolinate reductase (a dihydrodipicolinate reductase is hereinafter referred to as "DDPR", and a gene coding for a DDPR protein is hereinafter referred to as "dapB", if necessary), and the coryneform bacterium further harboring an enhanced DNA sequence coding for a dihydrodipicolinate synthase (a dihydrodipicolinate synthase is hereinafter referred to as "DDPS", and a gene coding for a DDPS protein is hereinafter referred to as "dapA", if necessary). Each of the genes for L-lysine biosynthesis used in the present invention is obtainable in accordance with certain methods as exemplified below.

(i) Preparation of mutant lysC

A DNA fragment containing mutant lysC can be prepared from a mutant strain in which synergistic feedback inhibition on the AK activity by L-lysine and L-threonine is substantially desensitized (International Publication No. WO 94/25605). Such a mutant strain can be obtained, for example, from a group of cells originating from a wild type strain of a coryneform bacterium subjected to a mutation treatment by applying an ordinary mutation treatment such as ultraviolet irradiation and treatment with a mutating agent such as N-methyl-N'-nitro-N-nitrosoguanidine. The AK activity can be measured by using a method described by Miyajima, R. et al., *The Journal of Biochemistry* (1968), 63(2), 139–148. The most preferred as such a mutant strain is represented by an L-lysine-producing bacterium AJ3445 (FERM P-1944) derived by a mutation treatment from a wild type strain of *Brevibacterium lactofermentum* ATCC 13869 (having its changed present name of *Corynebacterium alutamicum*).

Alternatively, mutant lysC is also obtainable by an in vitro mutation treatment of plasmid DNA containing wild type lysC. In another aspect, information is specifically known on mutation to desensitize synergistic feedback inhibition on AK by L-lysine and L-threonine (International Publication No. WO 94/25605). Accordingly, mutant lysC can be also prepared from wild type lysC on the basis of the information in accordance with, for example, the site-directed mutagenesis method.

A DNA fragment containing lysC can be prepared from chromosome of a coryneform bacterium by means of PCR. DNA primers are exemplified by single strand DNA's of 23-mer and 21-mer having nucleotide sequences shown in SEQ ID NOs: 10 and 11 in Sequence Listing in order to amplify, for example, a region of about 1,643 bp coding for lysC based on a sequence known for *Corynebacterium glutamicum* (see *Molecular Microbiology* (1991), 5(5), 1197–1204; *Mol. Gen. Genet.* (1990), 224, 317–324). Synthesis of DNA, PCR, and preparation of a plasmid carrying obtained lysC can be performed in the same manner as those for lysA described above.

Wild type lysC is obtained when lysC is isolated from an AK wild type strain, while mutant lysC is obtained when lysC is isolated from an AK mutant strain in accordance with the method as described above.

An example of a nucleotide sequence of a DNA fragment containing wild type lysC is shown in SEQ ID NO: 12 in Sequence Listing. An amino acid sequence of α-subunit of a wild type AK protein is deduced from the nucleotide sequence, and is shown in SEQ ID NO: 13 in Sequence Listing together with the DNA sequence. Only the amino acid sequence is shown in SEQ ID NO: 14. An amino acid sequence of β-subunit of the wild type AK protein is deduced from the nucleotide sequence of DNA, and is shown in SEQ ID NO: 15 in Sequence Listing together with the DNA sequence. Only the amino acid sequence is shown in SEQ ID NO: 16. In each of the subunits, GTG is used as an initiation codon, and a corresponding amino acid is represented by methionine. However, this representation refers to methionine, valine, or formylmethionine.

The mutant lysC used in the present invention is not specifically limited provided that it codes for AK in which synergistic feedback inhibition by L-lysine and L-threonine is desensitized. However, the mutant lysC is exemplified by one including mutation in which a 279th alanine residue as counted from the N-terminal is changed into an amino acid residue other than alanine and other than acidic amino acid in the α-subunit, and a 30th alanine residue is changed into an amino acid residue other than alanine and other than acidic amino acid in the β-subunit in the amino acid sequence of the wild type AK. The amino acid sequence of the wild type AK specifically includes the amino acid sequence shown in SEQ ID NO: 14 in Sequence Listing as the α-subunit, and the amino acid sequence shown in SEQ ID NO: 16 in Sequence Listing as the β-subunit.

Those preferred as the amino acid residue other than alanine and other than acidic amino acid include threonine, arginine, cysteine, phenylalanine, proline, serine, tyrosine, and valine residues.

The codon corresponding to an amino acid residue to be substituted is not specifically limited for its type provided that it codes for the amino acid residue. It is assumed that the amino acid sequence of possessed wild type AK may slightly differ depending on the difference in bacterial species and bacterial strains. AK's, which have mutation based on, for example, substitution, deletion, or insertion of one or more amino acid residues at one or more positions irrelevant to the enzyme activity as described above, can be also used for the present invention. Other AK's, which have mutation based on, for example, substitution, deletion, or insertion of other one or more amino acid residues, can be also used provided that no influence is substantially exerted on the AK activity, and on the desensitization of synergistic feedback inhibition by L-lysine and L-threonine.

An AJ12691 strain obtained by introducing a mutant lysc plasmid p399AK9B into an AJ12036 strain (FERM BP-734) as a wild type strain of *Brevibacterium lactofermentum* has been deposited on Apr. 10, 1992 under an accession number of FERM P-12918 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan), transferred to international deposition based on the Budapest Treaty on Feb. 10, 1995, and deposited under an accession number of FERM BP-4999.

(ii) Preparation of dapB

A DNA fragment containing dapB can be prepared from chromosome of a coryneform bacterium by means of PCR. The DNA donor is not specifically limited, however, it is exemplified by Brevibacterium lactofermentum ATCC 13869 strain.

A DNA sequence coding for DDPR is known for *Brevibacterium lactofermentum* (*Journal of Bacteriology*, 175(9), 2743–2749 (1993)), on the basis of which DNA primers for PCR can be prepared. Such DNA primers are specifically exemplified by DNA's of 23-mers respectively having nucleotide sequences shown in SEQ ID NOs: 21 and 22 in Sequence Listing. Synthesis of DNA, PCR, and preparation of a plasmid carrying obtained dapB can be performed in the same manner as those for lysC described above.

A nucleotide sequence of a DNA fragment containing dapB and an amino acid sequence deduced from the nucleotide sequence are illustrated in SEQ ID NO: 23. Only the amino acid sequence is shown in SEQ ID NO: 24. In addition to DNA fragments coding for this amino acid sequence, the present invention can equivalently use DNA fragments coding for amino acid sequences substantially the same as the amino acid sequence shown in SEQ ID NO: 24, namely amino acid sequences having mutation based on, for example, substitution, deletion, or insertion of one or more amino acids provided that there is no substantial influence on the DDPR activity.

A transformant strain AJ13107 obtained by introducing a plasmid pCRDAPB carrying dapB obtained in Example described later on into *E. coli* JM109 strain has been internationally deposited since May 26, 1995 under an accession number of FERM BP-5114 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan) based on the Budapest Treaty.

(iii) Preparation of dapA

A DNA fragment containing dapA can be prepared from chromosome of a coryneform bacterium by means of PCR. The DNA donor is not specifically limited, however, it is exemplified by *Brevibacterium lactofermentum* ATCC 13869 strain.

A DNA sequence coding for DDPS is known for *Corynebacterium glutamicum* (see *Nucleic Acids Research,* 18(21), 6421 (1990); EMBL accession No. X53993), on the basis of which DNA primers for PCR can be prepared. Such DNA primers are specifically exemplified by DNA's of 23-mers respectively having nucleotide sequences shown in SEQ ID NOs: 17 and 18 in Sequence Listing. Synthesis of DNA, PCR, and preparation of a plasmid carrying obtained dapA can be performed in the same manner as those for lysC described above.

A nucleotide sequence of a DNA fragment containing dapA and an amino acid sequence deduced from the nucleotide sequence are exemplified in SEQ ID NO: 23. Only the amino acid sequence is shown in SEQ ID NO: 24. In addition to DNA fragments coding for this amino acid sequence, the present invention can equivalently use DNA fragments coding for amino acid sequences substantially the same as the amino acid sequence shown in SEQ ID NO: 24, namely amino acid sequences having mutation based on, for example, substitution, deletion, or insertion of one or more amino acids provided that there is no substantial influence on the DDPS activity.

A transformant strain AJ13106 obtained by introducing a plasmid pCRDAPA carrying dapA obtained in Example described later on into *E. coli* JM109 strain has been internationally deposited since May 26, 1995 under an accession number of FERM BP-5113 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan) based on the Budapest Treaty.

In a specified embodiment, in order to enhance lysA and ddh in the L-lysine-producing coryneform bacterium as described above, the genes are introduced into the host by using a plasmid vector, transposon or phage vector or the like. Upon the introduction, it is expected to make enhancement to some extent even by using a low copy type vector. However, it is preferred to use a multiple copy type vector. Such a vector includes, for example, plasmid vectors, pAJ655, pAJ1844, pAJ611, pAJ3148, and pAJ440 described above. Besides, transposons derived from coryneform bacteria are described in International Publication Nos. WO 92/02627 and WO 93/18151; European Patent Publication No. 445385; Japanese Patent Application Laid-open No. 6-46867; Vertes, A. A. et al., *Mol. Microbiol.,* 11, 739–746 (1994); Bonamy, C., et al., *Mol. Microbiol.,* 14, 571–581 (1994); Vertes, A. A. et al., *Mol. Gen. Genet.,* 245, 397–405 (1994); Jagar, W. et al., *FEMS Microbiology Letters,* 126, 1–6 (1995); Japanese Patent Application Laid-open Nos. 7-107976 and 7-327680 and the like.

A coryneform bacterium enhanced in lysA and ddh according to the present invention can be obtained, for example, by introducing, into a host coryneform bacterium, a recombinant DNA containing lysA and ddh and being autonomously replicable in cells of coryneform bacteria. The recombinant DNA can be obtained, for example, by inserting lysA and ddh into a vector such as plasmid vector, transposon or phage vector as described above.

Each of the genes of lysA and ddh may be successively introduced into the host by using different vectors respectively. Alternatively, two species of the genes may be introduced together by using a single vector. When different vectors are used, the genes may be introduced in any order, however, it is preferred to use vectors which have a stable sharing and harboring mechanism in the host, and which are capable of co-existing with each other.

In the case in which a plasmid is used as a vector, the recombinant DNA can be introduced into the host in accordance with an electric pulse method (Sugimoto et al., Japanese Patent Application Laid-open No. 2-207791). Amplification of a gene using transposon can be performed by introducing a plasmid carrying a transposon into the host cell and inducing transposition of the transposon.

Also, when mutant lysC, dapA and dapB are introduced into coryneform bacterium, each of the genes and lysA and ddh may be successively introduced into the host by using different vectors respectively or, alternatively, two or more species of the genes may be introduced together by using a single vector.

<3> Method for producing L-lysine

L-Lysine can be efficiently produced by cultivating, in an appropriate medium, the coryneform bacterium comprising the enhanced genes for L-lysine biosynthesis as described above to allow L-lysine to be produced and accumulated in a culture, and collecting L-lysine from the culture.

The medium to be used is exemplified by an ordinary medium containing a carbon source, a nitrogen source, inorganic ions, and optionally other organic components.

As the carbon source, it is possible to use sugars such as glucose, fructose, sucrose, molasses, and starch hydrolysate; and organic acids such as fumaric acid, citric acid, and succinic acid.

As the nitrogen source, it is possible to use inorganic ammonium salts such as ammonium sulfate, ammonium chloride, and ammonium phosphate; organic nitrogen such as soybean hydrolysate; ammonia gas; and aqueous ammonia.

As organic trace nutrient sources, it is desirable to contain required substances such as vitamin $B_1$ and L-homoserine or yeast extract or the like in appropriate amounts. Other than the above, potassium phosphate, magnesium sulfate, iron ion, manganese ion and so on are added in small amounts, if necessary.

Cultivation is preferably carried out under an aerobic condition for about 30 to 90 hours. The cultivation temperature is preferably controlled at 25° C. to 37° C., and pH is preferably controlled at 5 to 8 during cultivation. Inorganic or organic, acidic or alkaline substances, or ammonia gas or the like can be used for pH adjustment. L-lysine can be collected from a culture by combining an ordinary ion exchange resin method, a precipitation method, and other known methods.

EXAMPLES

The present invention will be more specifically explained below with reference to Examples.

EXAMPLE 1: Preparation of lysA from *Brevibacterium lactofermentum*

<1> Preparation of lysA and construction of plasmid carrying lysA

A wild type strain ATCC 13869 of *Brevibacterium lactofermentum* was used as a chromosomal DNA donor. Chromosomal DNA was prepared from the ATCC 13869 strain in accordance with an ordinary method. A DNA fragment containing argS, lysA, and a promoter of an operon containing them was amplified from the chromosomal DNA in accordance with PCR. As for DNA primers used for amplification, synthetic DNA's of 23-mers having nucleotide sequences shown in SEQ ID NOs: 1 and 2 in Sequence Listing respectively were used in order to amplify a region of about 3.6 kb coding for arginyl-tRNA synthase and DDC on the basis of a sequence known for *Corynebacterium glutamicum* (see *Molecular Microbiology*, 4(11), 1819–1830 (1990); *Molecular and General Genetics*, 212, 112–119 (1988)).

DNA was synthesized in accordance with an ordinary method by using DNA synthesizer model 380B produced by Applied Biosystems and using the phosphoamidite method (see *Tetrahedron Letters* (1981), 22, 1859).

The gene was amplified by PCR by using DNA Thermal Cycler Model PJ2000 produced by Takara Shuzo, and using Taq DNA polymerase in accordance with a method designated by the supplier. pHSG399 was used as a cloning vector for the amplified gene fragment of 3,579 bp. pHSG399 was digested with a restriction enzyme SmaI (produced by Takara Shuzo), and was ligated with the DNA fragment containing amplified lysA. A plasmid obtained as described above, which had lysA originating from ATCC 13869, was designated as p399LYSA.

A DNA fragment containing lysA was extracted by digesting p399LYSA with KpnI (produced by Takara Shuzo) and BamHI (produced by Takara Shuzo). This DNA fragment was ligated with pHSG299 having been digested with KpnI and BamHI. An obtained plasmid was designated as p299LYSA. The process of construction of p299LYSA is shown in FIG. 1.

Figure 2:
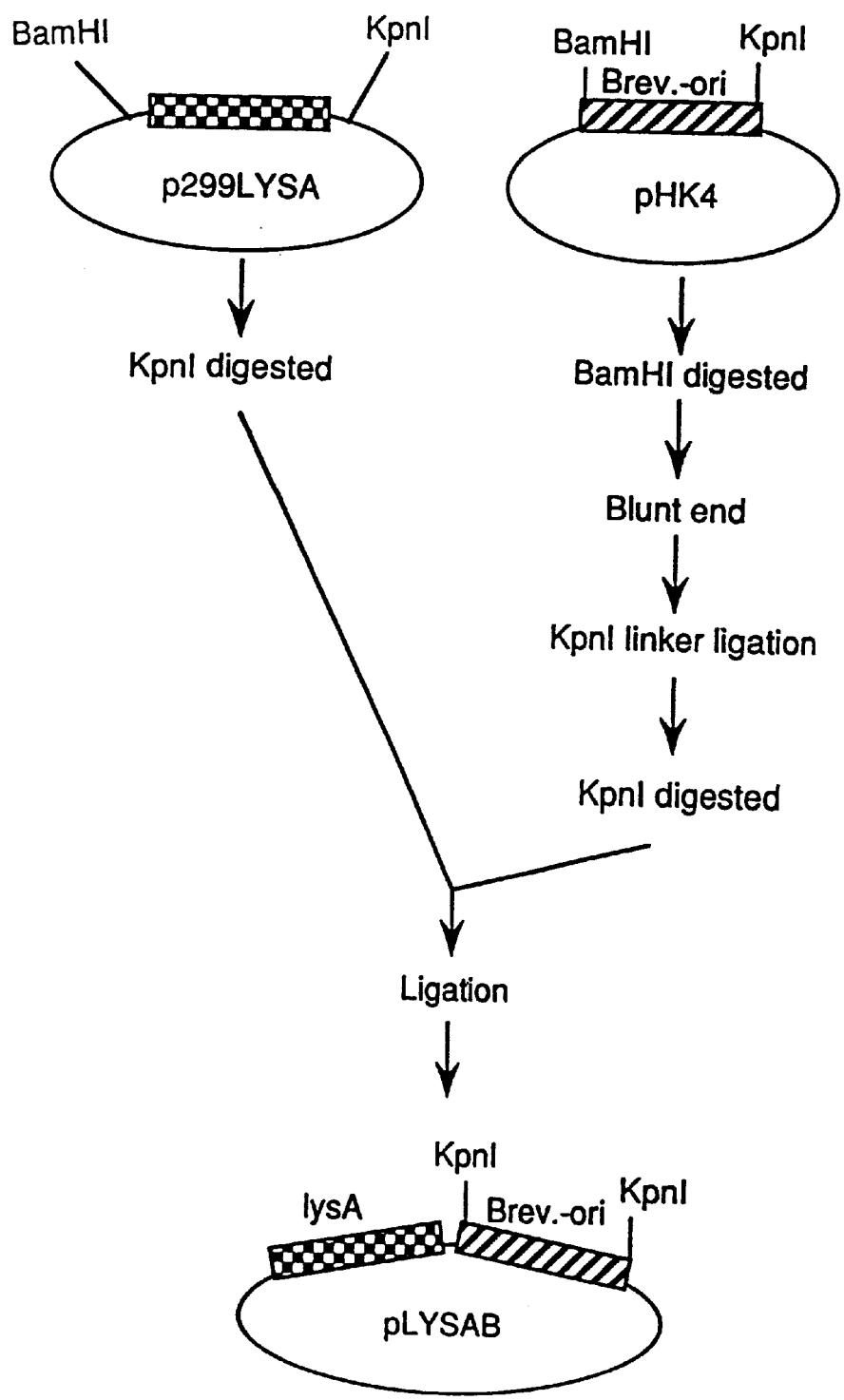
FIG. 2 illustrates a process of construction of a plasmid pLYSAB carrying lysA and Brevi.-ori.

A DNA fragment (hereinafter referred to as "Brevi.-ori") having an ability to make a plasmid autonomously replicable in bacteria belonging to the genus Corynebacterium was introduced into p299LYSA to prepare plasmids carrying lysA autonomously replicable in bacteria belonging to the genus Corynebacterium. Brevi.-ori was prepared from a plasmid vector pHK4 containing Brevi.-ori and autonomously replicable in cells of both *Escherichia coli* and bacteria belonging to the genus Corynebacterium. pHK4 was constructed by digesting pHC4 with KpnI (produced by Takara Shuzo) and BamHI (produced by Takara Shuzo), extracting a Brevi.-ori fragment, and ligating it with pHSG298 having been also digested with KpnI and BamHI (see Japanese Patent Application Laid-open No. 5-7491). pHK4 gives kanamycin resistance to a host. *Escherichia coli* HB101 harboring pHK4 was designated as *Escherichia coli* AJ13136, and deposited on Aug. 1, 1995 under an accession number of FERM BP-5186 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan).

pHK4 was digested with a restriction enzyme BamHI, and cleaved ends were blunted. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p299LYSA having been also digested with KpnI to prepare a plasmid carrying lysA autonomously replicable in coryneform bacteria. The prepared plasmid was designated as pLYSAB. The process of construction of pLYSAB is shown in FIG. 2.

<2> Determination of nucleotide sequence of lysA from *Brevibacterium lactofermentum*

Plasmid DNA of p299LYSA was prepared, and nucleotide sequence determination was performed in accordance with a method of Sanger et al. (for example, F. Sanger et al., *Proc. Natl. Acad. Sci.*, 74, 5463 (1977)). A determined nucleotide sequence and an amino acid sequence deduced to be encoded by the nucleotide sequence are shown in SEQ ID NO: 3. Concerning the nucleotide sequence, an amino acid sequence encoded by argS and an amino acid sequence encoded by lysA are shown in SEQ ID NOs: 4 and 5 respectively.

EXAMPLE 2: Preparation of ddh from *Brevibacterium lactofermentum*

A ddh gene was obtained by amplifying the ddh gene from chromosomal DNA of *Brevibacterium lactofermentum* ATCC 13869 in accordance with the PCR method by using two oligonucleotide primers (SEQ ID NOs: 6, 7) prepared on the basis of a known nucleotide sequence of a ddh gene of *Corynebacterium glutamicum* (Ishino, S. et al., *Nucleic Acids Res.*, 15, 3917 (1987)). An obtained amplified DNA fragment was digested with EcoT22I and AvaI, and cleaved ends were blunted. After that, the fragment was inserted into a SmaI site of pMW119 to obtain a plasmid pDDH.

Next, pDDH was digested with SalI and EcoRI, followed by blunt end formation. After that, an obtained fragment was ligated with pUC18 having been digested with SmaI. A plasmid thus obtained was designated as pUC18DDH.

Figure 3:
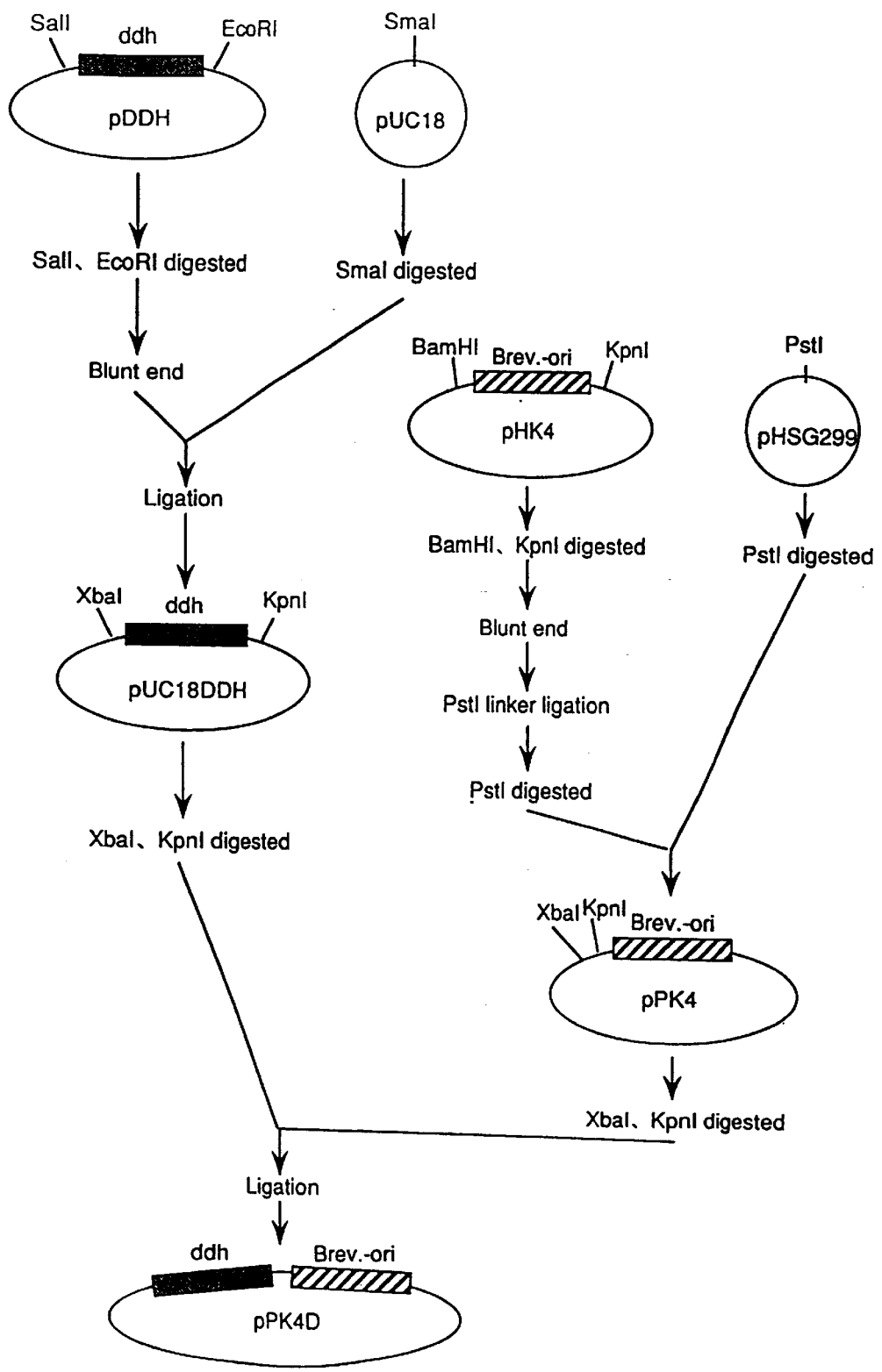
FIG. 3 illustrates a process of construction of a plasmid pPK4D carrying ddh and Brevi.-ori.

Brevi.-ori was introduced into pUC18DDH to construct a plasmid carrying ddh autonomously replicable in coryneform bacteria. pHK4 was digested with restriction enzymes KpnI and BamHI, and cleaved ends were blunted. Blunt end formation was performed by using DNA Blunting kit (produced by Takara Shuzo) in accordance with a designated method. After the blunt end formation, a phosphorylated PstI linker (produced by Takara Shuzo) was ligated so that it was inserted into a PstI site of pHSG299. A plasmid constructed as described above was designated as pPK4. Next, pUC18DDH was digested with XbaI and KpnI, and a generated fragment was ligated with pPK4 having been digested with KpnI and XbaI. Thus a plasmid carrying ddh autonomously replicable in coryneform bacteria was constructed. This plasmid was designated as pPK4D. The process of construction of pPK4D is shown in FIG. 3.

EXAMPLE 3: Construction of Plasmid Carrying Both of ddh and lysA

Figure 4:
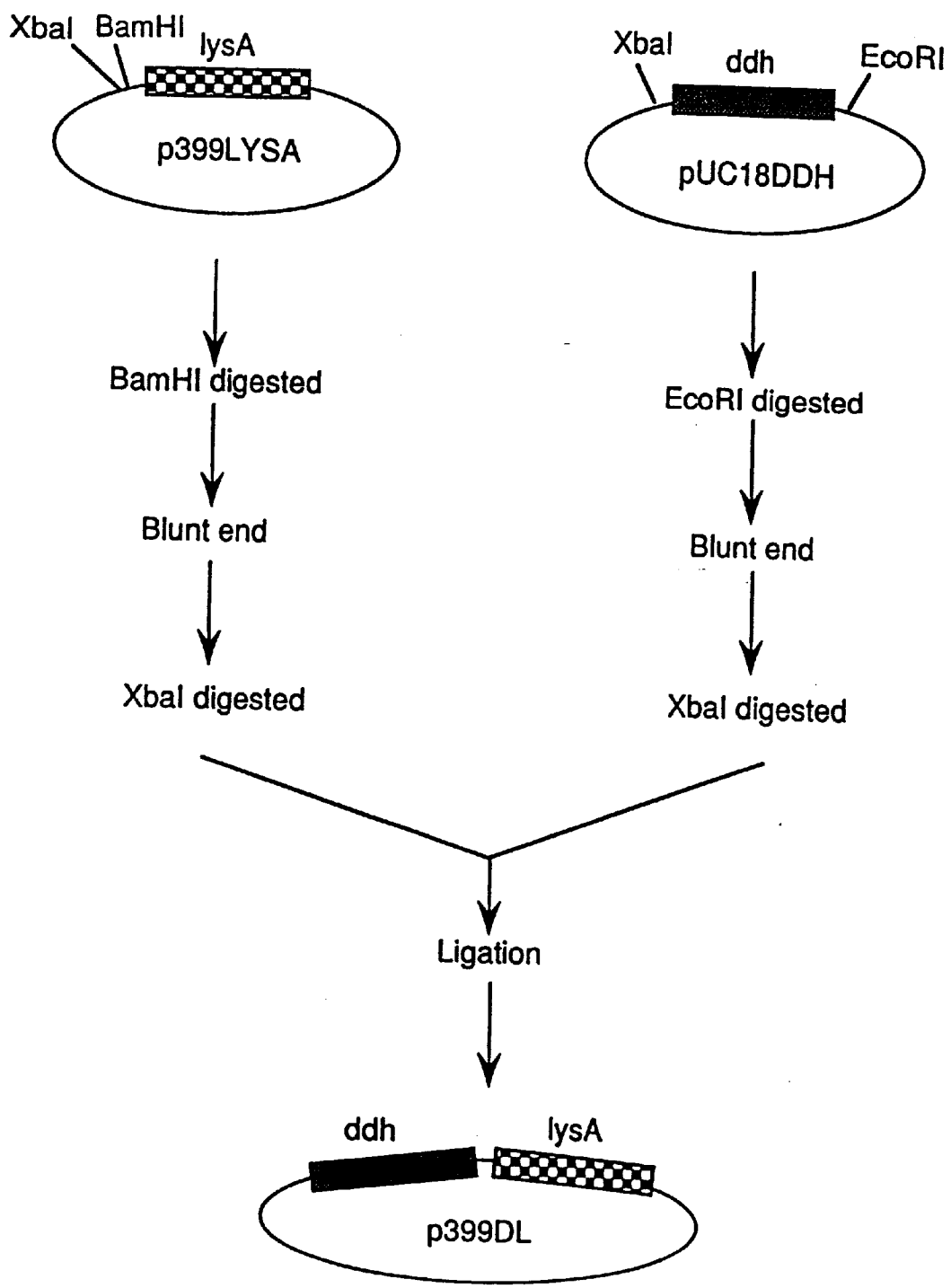
FIG. 4 illustrates a process of construction of a plasmid p399DL carrying ddh and lysA.

The plasmid pUC18DDH carrying ddh was digested with EcoRI and then blunt-ended and further digested with XbaI to extract a DNA fragment containing ddh. This ddh fragment was ligated with the plasmid p399LYSA carrying lysA having been digested with BamHI and then blunt-ended and further having been digested with XbaI. An obtained plasmid was designated as p399DL. The process of construction of p399DL is shown in FIG. 4.

Figure 5:
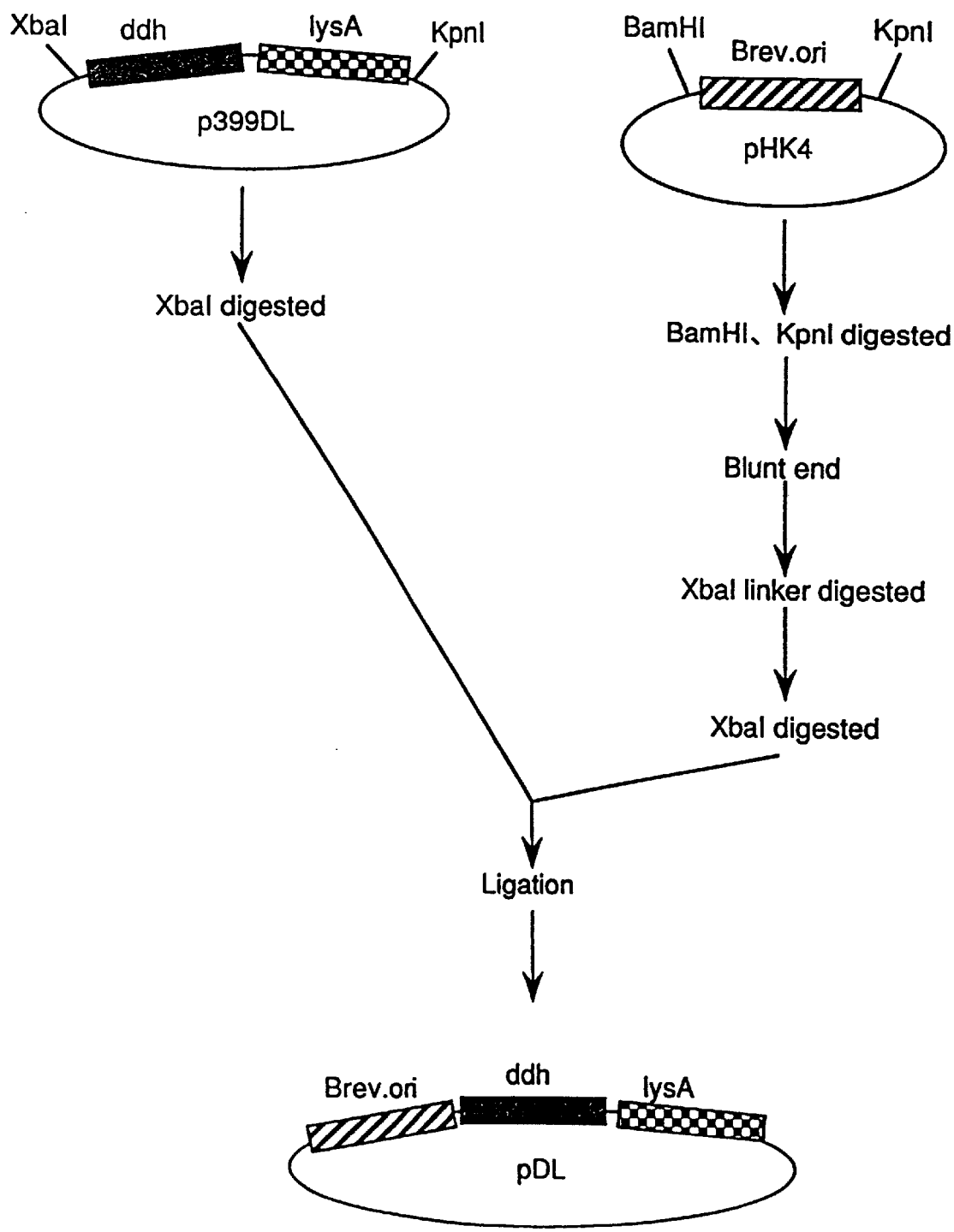
FIG. 5 illustrates a process of construction of a plasmid pDL carrying ddh, lysA and Brevi.-ori.

Next, Brevi.-ori was introduced into p399DL. pHK4 was digested with XbaI and BamHI, and cleaved ends were blunted. After the blunt end formation, a phosphorylated XbaI linker was ligated to make modification so that the DNA fragment corresponding to the Brevi.-ori portion might be excised from pHK4 by digestion with only XbaI. This plasmid was digested with XbaI, and the generated Brevi.-ori DNA fragment was ligated with p399DL having been also digested with XbaI to construct a plasmid containing ddh and lysA autonomously replicable in coryneform bacteria. The constructed plasmid was designated as pDL. The process of construction of pDL is shown in FIG. 5.

EXAMPLE 4: Preparation of Mutant lysC, dapA and dapB from *Brevibacterium lactofermentum*

<1> Preparation of Wild Type lysC Gene and Mutant lysC Gene from *Brevibacterium lactofermentum* (1) Preparation of wild type and mutant lysC's and preparation of plasmids carrying them A strain of *Brevibacterium lactofermentum* ATCC 13869, and an L-lysine-producing mutant strain AJ3445 (FERM P-1944) obtained from the ATCC 13869 strain by a mutation treatment were used as chromosomal DNA donors. The AJ3445 strain had been subjected to mutation so that lysC was changed to involve substantial desensitization from concerted inhibition by lysine and threonine (*Journal of Biochemistry*, 68, 701–710 (1970)).

A DNA fragment containing lysC was amplified from chromosomal DNA in accordance with the PCR method (polymerase chain reaction; see White, T. J. et al., *Trends Genet.*, 5, 185 (1989)). As for DNA primers used for amplification, single strand DNA's of 23-mer and 21-mer having nucleotide sequences shown in SEQ ID NOs: 10 and 11 were synthesized in order to amplify a region of about 1,643 bp coding for lysC on the basis of a sequence known for *Corynebacterium alutamicum* (see *Molecular Microbiology* (1991), 5(5), 1197–1204; and *Mol. Gen. Genet.* (1990), 224, 317–324).

An amplified gene fragment of 1,643 kb was confirmed by agarose gel electrophoresis. After that, the fragment excised from the gel was purified in accordance with an ordinary method, and it was digested with restriction enzymes NruI (produced by Takara Shuzo) and EcoRI (produced by Takara Shuzo).

pHSG399 (see Takeshita, S. et al., *Gene* (1987), 61, 63–74) was used as a cloning vector for the gene fragment. pHSG399 was digested with restriction enzymes SmaI (produced by Takara Shuzo) and EcoRI, and it was ligated with the amplified lysC fragment. DNA was ligated by using DNA ligation kit (produced by Takara Shuzo) in accordance with a designated method. Thus plasmids were prepared, in which the lysC fragments amplified from chromosomes of *Brevibacterium lactofermentum* were ligated with pHSG399 respectively. A plasmid carrying lysC from ATCC 13869 (wild type strain) was designated as p399AKY, and a plasmid carrying lysC from AJ3463 (L-lysine-producing bacterium) was designated as p399AK9.

Brevi.-ori was introduced into the prepared p399AKY and p399AK9 respectively to construct plasmids carrying lysC autonomously replicable in coryneform bacteria.

pHK4 was digested with restriction enzymes KpnI and BamHI (produced by Takara Shuzo), and cleaved ends were blunted. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKY and p399AK9 having been also digested with BamHI to prepare plasmids carrying lysC autonomously replicable in coryneform bacteria.

Figure 6:
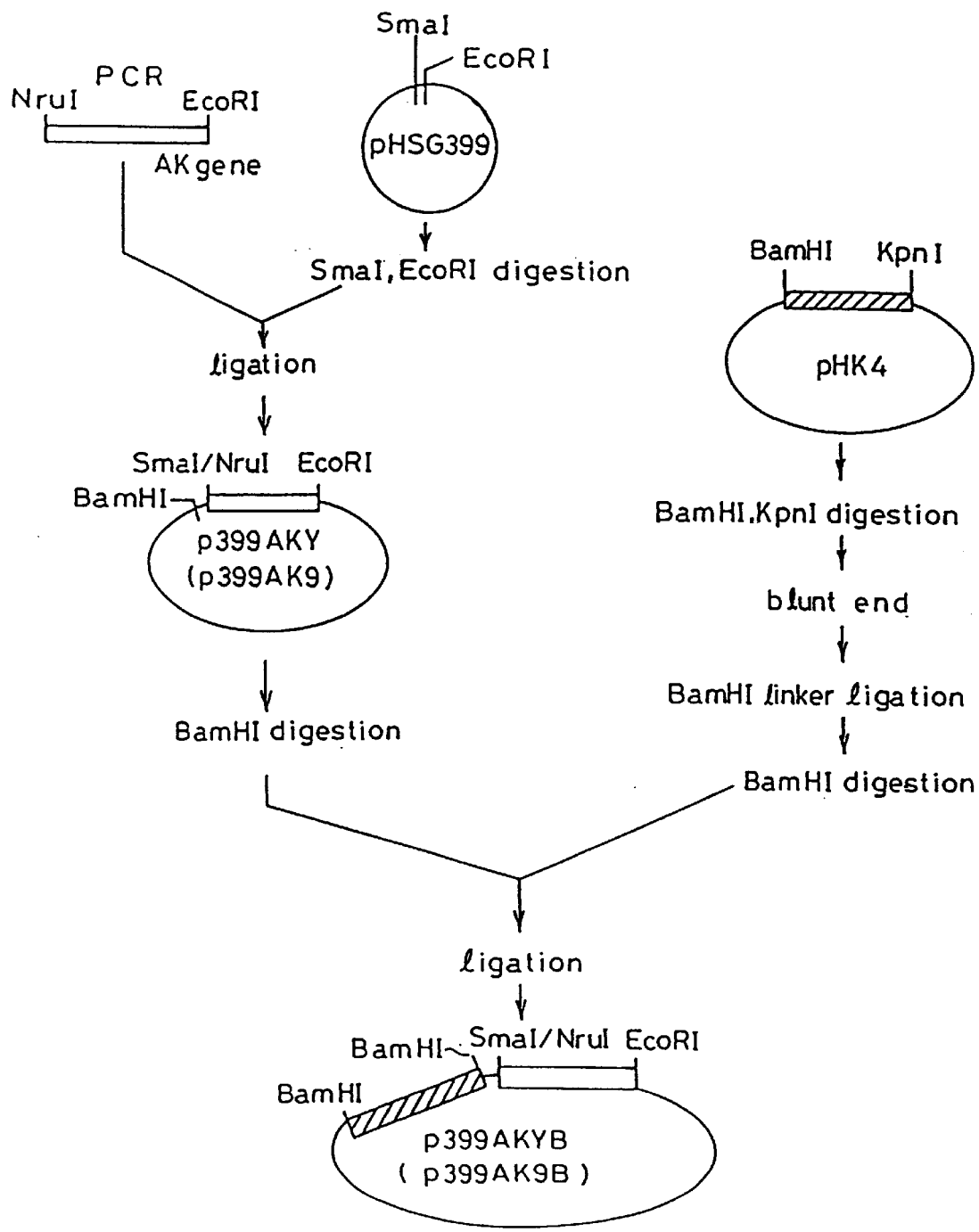
FIG. 6 illustrates a process of construction of plasmids p399AKYB and p399AK9B each carrying mutant lysC.

A plasmid carrying the wild type lysC gene originating from p399AKY was designated as p399AKYB, and a plasmid carrying the mutant lysC gene originating from p399AK9 was designated as p399AK9B. The process of construction of p399AK9B and p399AKYB is shown in FIG. 6. A strain AJ12691 obtained by introducing the mutant lysC plasmid p399AK9B into a wild type strain of *Brevibacterium lactofermentum* (AJ12036 strain, FERM BP-734) was deposited on Apr. 10, 1992 under an accession number of FERM P-12918 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan), transferred to international deposition based on the Budapest Treaty on Feb. 10, 1995, and deposited under an accession number of FERM BP-4999.

(2) Determination of nucleotide sequences of wild type lysC and mutant lysC from *Brevibacterium lactofermentum*

The plasmid p399AKY containing the wild type lysC and the plasmid p399AK9 containing the mutant lysC were prepared from the respective transformants to determine nucleotide sequences of the wild type and mutant lysC's. Nucleotide sequence determination was performed in accordance with a method of Sanger et al. (for example, F. Sanger et al., *Proc. Natl. Acad. Sci.*, 74, 5463 (1977)).

The nucleotide sequence of wild type lysC encoded by p399AKY is shown in SEQ ID NO: 12 in Sequence Listing. On the other hand, the nucleotide sequence of mutant lysC encoded by p399AK9 had only mutation of one nucleotide such that 1051st G was changed into A in SEQ ID NO: 12 as compared with wild type lysC. It is known that lysC of *Corynebacterium glutamicum* has two subunits ($\alpha$, $\beta$) encoded in an identical reading frame on an identical DNA strand (see Kalinowski, J. et al., *Molecular Microbiology* (1991) 5(5), 1197–1204). Judging from homology, it is expected that the gene sequenced herein also has two subunits ($\alpha$, $\beta$) encoded in an identical reading frame on an identical DNA strand.

An amino acid sequence of the $\alpha$-subunit of the wild type AK protein deduced from the nucleotide sequence of DNA is shown in SEQ ID NO: 13 together with the DNA sequence. Only the amino acid sequence is shown in SEQ ID NO: 14. An amino acid sequence of the $\beta$-subunit of the wild type AK protein deduced from the nucleotide sequence of DNA is shown in SEQ ID NO: 15 together with DNA. Only the amino acid sequence is shown in SEQ ID NO: 16. In each of the subunits, GTG is used as an initiation codon, and a corresponding amino acid is represented by methionine. However, this representation refers to methionine, valine, or formylmethionine.

On the other hand, mutation on the sequence of mutant lysC means occurrence of amino acid residue substitution such that a 279th alanine residue of the $\alpha$-subunit is changed into a threonine residue, and a 30th alanine residue of the $\beta$-subunit is changed into a threonine residue in the amino acid sequence of the wild type AK protein (SEQ ID NOs: 14, 16).

<2> Preparation of dapB from *Brevibacterium lactofermentum*

(1) Preparation of dapB and construction of plasmid carrying dapB

A wild type strain ATCC 13869 of *Brevibacterium lactofermentum* was used as a chromosomal DNA donor. Chromosomal DNA was prepared from the ATCC 13869 strain in accordance with an ordinary method. A DNA fragment containing dapB was amplified from the chromosomal DNA in accordance with PCR. As for DNA primers used for amplification, DNA's of 23-mers having nucleotide sequences shown in SEQ ID NOs: 17 and 18 in Sequence Listing respectively were synthesized in order to amplify a region of about 2.0 kb coding for DDPR on the basis of a sequence known for *Brevibacterium lactofermentum* (see *Journal of Bacteriolgy*, 157(9), 2743–2749 (1993)). Synthesis of DNA and PCR were performed in the same manner as described in Example 1. pCR-Script (produced by Invitrogen) was used as a cloning vector for the amplified gene fragment of 2,001 bp, and was ligated with the amplified dapB fragment. Thus a plasmid was constructed, in which the dapB fragment of 2,001 bp amplified from chromosome of *Brevibacterium lactofermentum* was ligated with pCR-Script. The plasmid obtained as described above, which had dapB originating from ATCC 13869, was designated as pCRDAPB. A transformant strain AJ13107 obtained by introducing pCRDAPB into *E. coli* JM109 strain has been internationally deposited since May 26, 1995 under an accession number of FERM BP-5114 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan) based on the Budapest Treaty.

A fragment of 1,101 bp containing a structural gene of DDPR was extracted by digesting pCRDAPB with EcoRV and SphI. This fragment was ligated with pHSG399 having been digested with HincII and SphI to prepare a plasmid. The prepared plasmid was designated as p399DPR.

Figure 7:
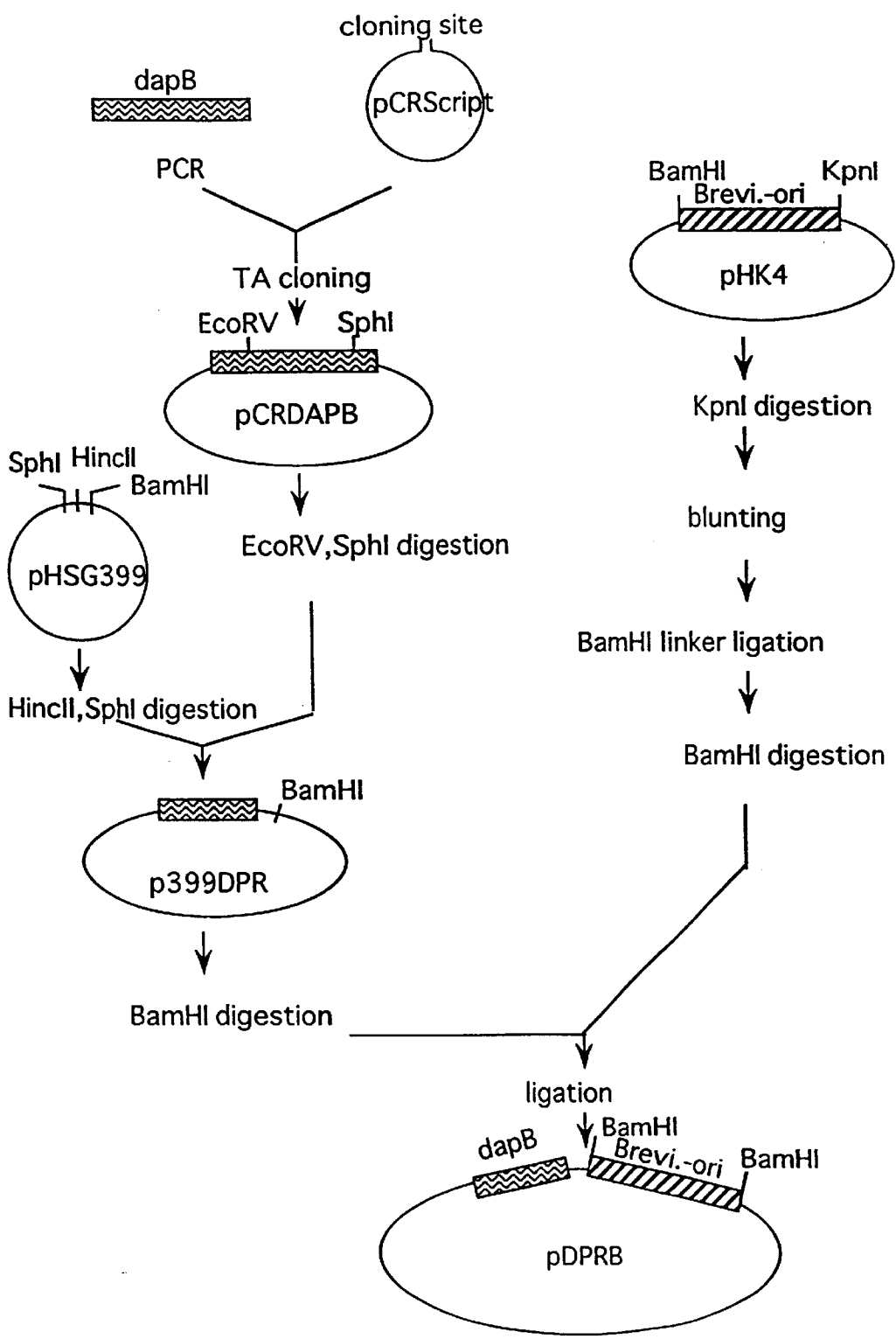
FIG. 7 illustrates a process of construction of a plasmid pDPRB carrying dapB and Brevi.-ori.

Brevi.-ori was introduced into the prepared p399DPR to construct a plasmid carrying dapB autonomously replicable in coryneform bacteria. pHK4 was digested with a restriction enzyme KpnI (produced by Takara Shuzo), and cleaved ends were blunted. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399DPR having been also digested with BamHI to prepare a plasmid containing dapB autonomously replicable in coryneform bacteria. The prepared plasmid was designated as pDPRB. The process of construction of pDPRB is shown in FIG. 7.

(2) Determination of nucleotide sequence of dapB from *Brevibacterium lactofermentum*

Plasmid DNA was prepared from the AJ13107 strain harboring p399DPR, and its nucleotide sequence was determined in the same manner as described in Example 1. A determined nucleotide sequence and an amino acid sequence deduced from the nucleotide sequence are shown in SEQ ID NO: 23. Only the amino acid sequence is shown in SEQ ID NO: 24.

<3> Preparation of dapA from *Brevibacterium lactofermentum*

(1) Preparation of dapA and construction of plasmid carrying dapA

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapA was amplified from the chromosomal DNA in accordance with PCR. As for DNA primers used for amplification, DNA's of 23-mers having nucleotide sequences shown in SEQ ID NOs: 17 and 18 in Sequence Listing respectively were synthesized in order to amplify a region of about 1.5 kb coding for DDPS on the basis of a sequence known for *Corynebacterium glutamicum* (see *Nucleic Acids Research*, 18(21), 6421 (1990); EMBL accession No. X53993). Synthesis of DNA and PCR were performed in the same manner as described in Example 1. pCR1000 (produced by Invitrogen, see *Bio/Technology*, 9, 657–663 (1991)) was used as a cloning vector for the amplified gene fragment of 1,411 bp, and was ligated with the amplified dapA fragment. Ligation of DNA was performed by using DNA ligation kit (produced by Takara Shuzo) in accordance with a designated method. Thus a plasmid was constructed, in which the dapA fragment of 1,411 bp amplified from chromosome of *Brevibacterium lactofermentum* was ligated with pCR1000. The plasmid obtained as described above, which had dapA originating from ATCC 13869, was designated as pCRDAPA.

A transformant strain AJ13106 obtained by introducing pCRDAPA into *E. coli* JM109 strain has been internationally deposited since May 26, 1995 under an accession number of FERM BP-5113 in National Institute of Bioscience and Human Technology of Agency of Industrial Science and Technology of Ministry of International Trade and Industry (postal code: 305, 1–3, Higashi 1-chome, Tsukuba-shi, Ibaraki-ken, Japan) based on the Budapest Treaty.

Figure 8:
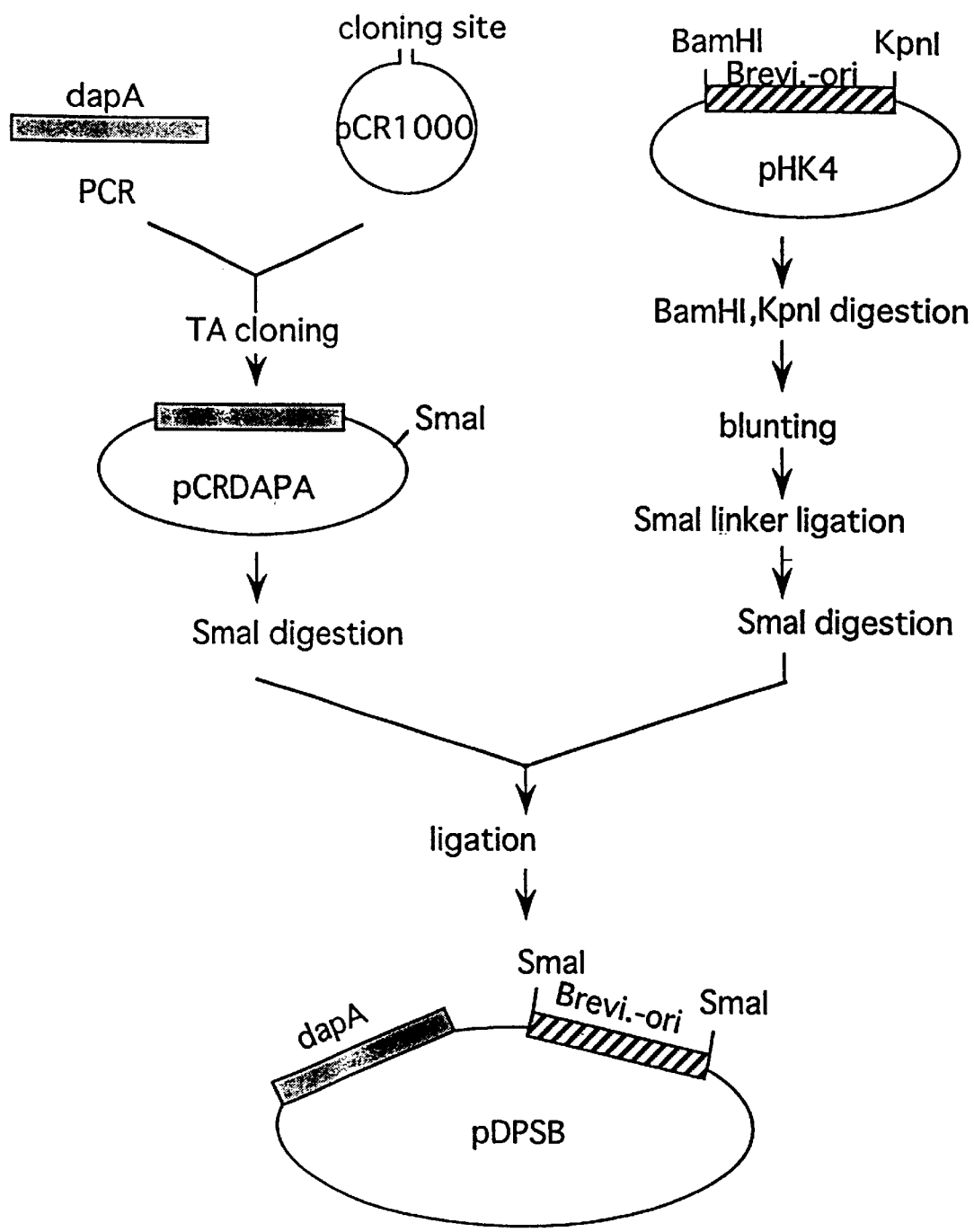
FIG. 8 illustrates a process of construction of a plasmid pDPSB carrying dapA and Brevi.-ori.

Brevi.-ori was introduced into the prepared pCRDAPA to construct a plasmid carrying dapA autonomously replicable in coryneform bacteria. pHK4 was digested with restriction enzymes KpnI and BamHI (produced by Takara Shuzo), and cleaved ends were blunted. Blunt end formation was performed by using DNA Blunting kit (produced by Takara Shuzo) in accordance with a designated method. After the blunt end formation, a phosphorylated SmaI linker (produced by Takara Shuzo) was ligated to make modification so that the DNA fragment corresponding to the Brevi.-ori portion might be excised from pHK4 by digestion with only SmaI. This plasmid was digested with SamI, and the generated Brevi.-ori DNA fragment was ligated with pCRDAPA having been also digested with SmaI to prepare a plasmid carrying dapA autonomously replicable in coryneform bacteria. This plasmid was designated as pDPSB. The process of construction of pDPSB(Km$^r$) is shown in FIG. 8.

(2) Determination of nucleotide sequence of dapA from *Brevibacterium lactofermentum*

Plasmid DNA was prepared from the AJ13106 strain harboring pCRDAPA, and its nucleotide sequence was determined in the same manner as described in Example 1. A determined nucleotide sequence and an amino acid sequence deduced from the nucleotide sequence are shown in SEQ ID NO: 19. Only the amino acid sequence is shown in SEQ ID NO: 20.

<4> Construction of Plasmid Carrying Both of Mutant lysC and dapA

Figure 9:
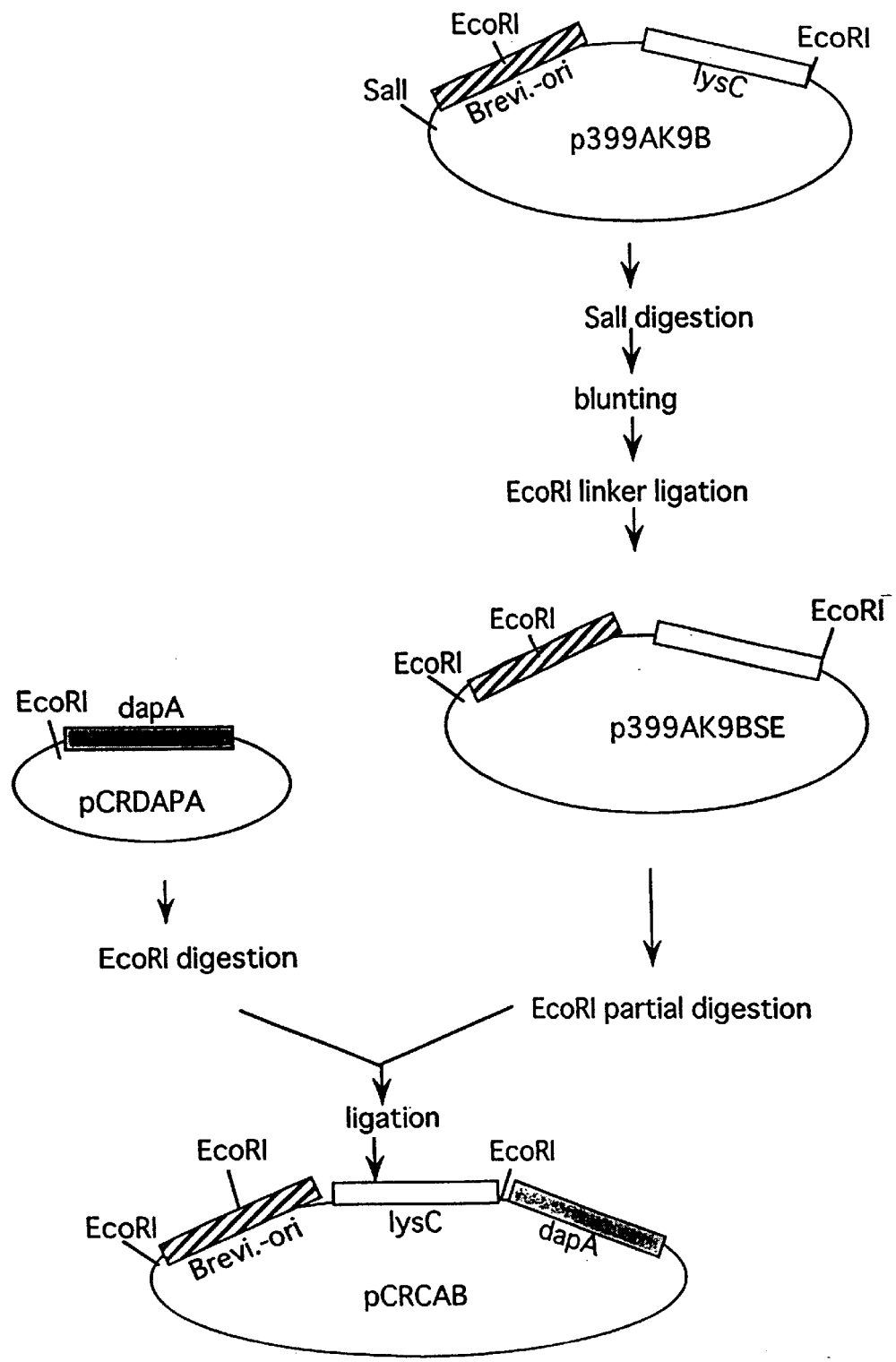
FIG. 9 illustrates a process of construction of a plasmid pCRCAB carrying lysC, dapB and Brevi.-ori.

A plasmid carrying mutant lysC, dapA, and replication origin of coryneform bacteria was constructed from the plasmid pCRDAPA carrying dapA and the plasmid p399AK9B carrying mutant lysC and Brevi.-ori. p399AK9B was completely digested with SalI, and then it was blunt-ended. An EcoRI linker was ligated therewith to construct a plasmid in which the SalI site was modified into an EcoRI site. The obtained plasmid was designated as p399AK9BSE. The mutant lysC and Brevi.-ori were excised as one fragment by partially digesting p399AK9BSE with EcoRI. This fragment was ligated with pCRDAPA having been digested with EcoRI. An obtained plasmid was designated as pCR-CAB. This plasmid is autonomously replicable in E. coli and coryneform bacteria, and it gives kanamycin resistance to a host, the plasmid carrying both of mutant lysC and dapA. The process of construction of pCRCAB is shown in FIG. 9.

<5> Construction of Plasmid Carrying Both of Mutant lysC and dapB

A plasmid carrying mutant lysC and dapB was constructed from the plasmid p399AK9 carrying mutant lysC and the plasmid p399DPR carrying dapB. A fragment of 1,101 bp containing a structural gene of DDPR was extracted by digesting p399DPR with EcoRV and SphI. This fragment was ligated with p399AK9 having been digested with SalI and then blunt-ended and having been further digested with SphI to construct a plasmid carrying both of mutant lysC and dapB. This plasmid was designated as p399AKDDPR.

Figure 10:
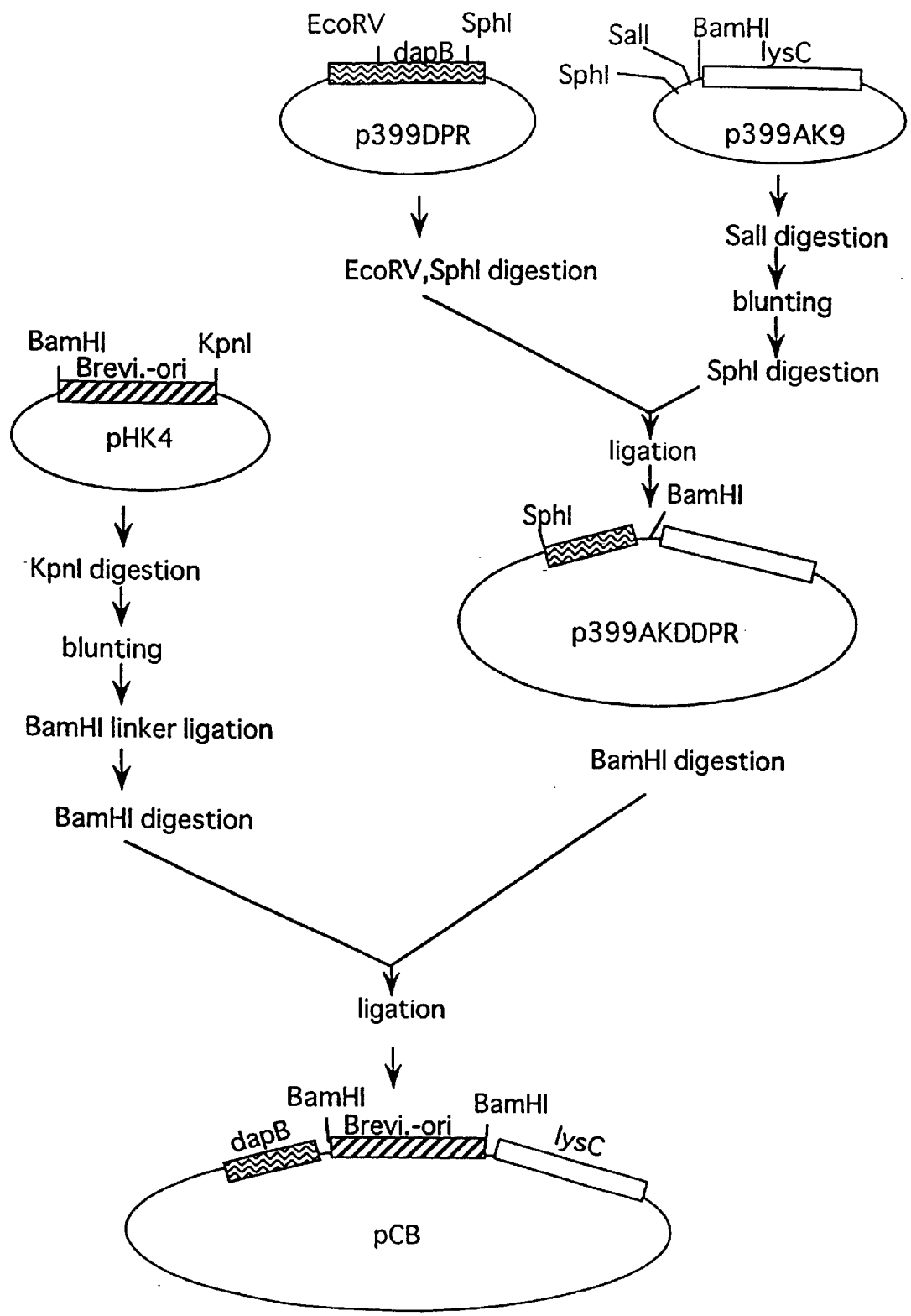
FIG. 10 illustrates a process of construction of a plasmid pCB carrying mutant lysC, dapB, and Brevi.-ori.

Next, Brevi.-ori was introduced into the obtained p399AKDDPR. The plasmid pHK4 containing Brevi.-ori was digested with a restriction enzyme KpnI (produced by Takara Shuzo), and cleaved ends were blunted. Blunt end formation was performed by using DNA Blunting kit (produced by Takara Shuzo) in accordance with a designated method. After the blunt end formation, a phosphorylated BamHI linker (produced by Takara Shuzo) was ligated to make modification so that the DNA fragment corresponding to the Brevi.-ori portion might be excised from pHK4 by digestion with only BamHI. This plasmid was digested with BamHI, and the generated Brevi.-ori DNA fragment was ligated with p399AKDDPR having been also digested with BamHI to construct a plasmid carrying mutant lysC and dapB autonomously replicable in coryneform bacteria. The constructed plasmid was designated as pCB. The process of construction of pCB is shown in FIG. 10.

<6> Construction of Plasmid Carrying Both of dapA and dapB

The plasmid pCRDAPA carrying dapA was digested with KpnI and EcoRI to extract a DNA fragment containing dapA and the fragment was ligated with the vector plasmid pHSG399 having been digested with KpnI and EcoRI. An obtained plasmid was designated as p399DPS.

On the other hand, the plasmid pCRDAPB carrying dapB was digested with SacII and EcoRI to extract a DNA fragment of 2.0 kb containing a region coding for DDPR and the fragment was ligated with p399DPS having been digested with SacII and EcoRI to construct a plasmid carrying both of dapA and dapB. The obtained plasmid was designated as p399AB.

Figure 11:
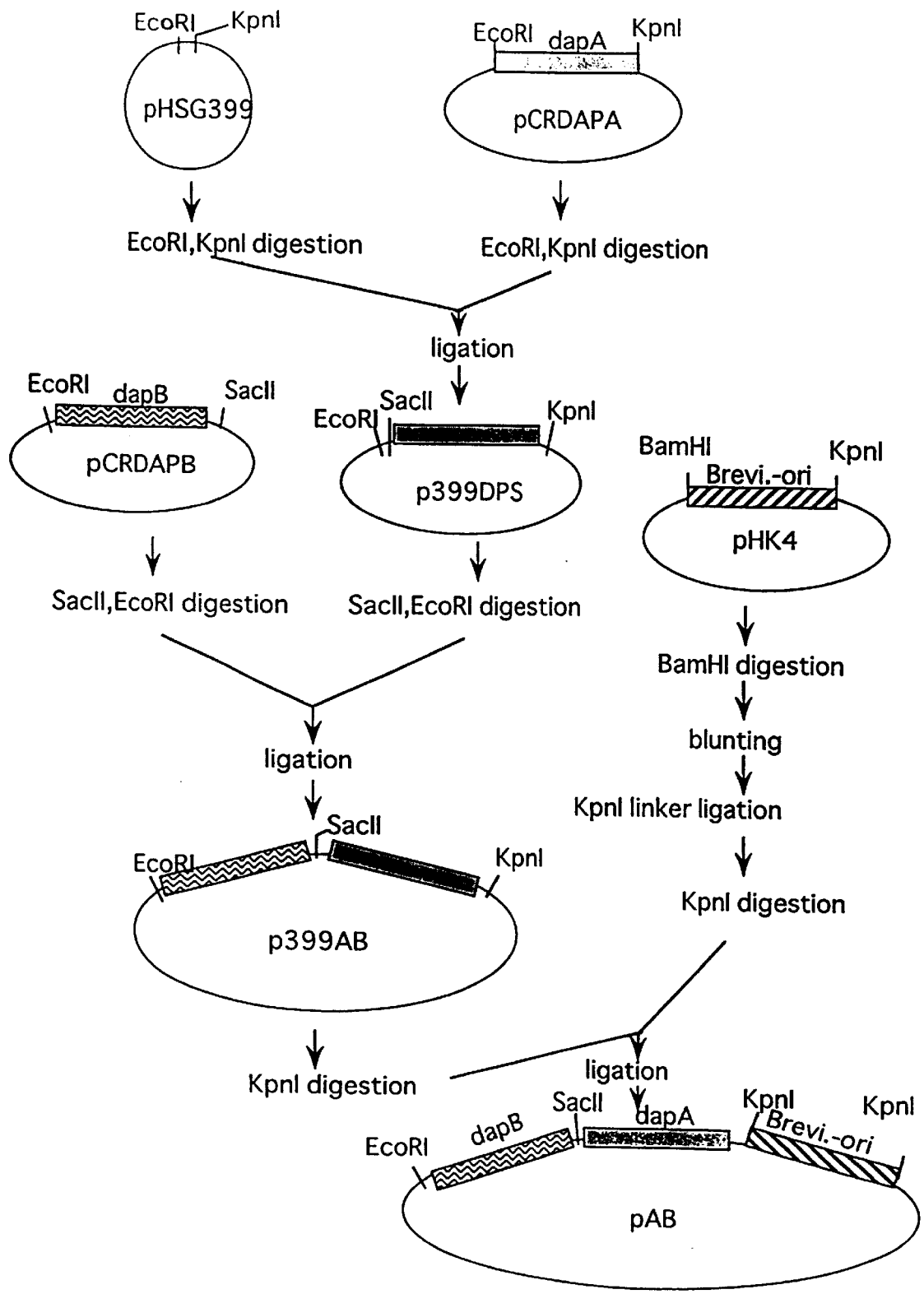
FIG. 11 illustrates a process of construction of a plasmid pAB carrying dapA, dapB and Brevi.-ori.

Next, Brevi.-ori was introduced into p399AB. pHK4 carrying Brevi.-ori was digested with a restriction enzyme BamHI (produced by Takara Shuzo), and cleaved ends were blunted. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p399AB having been also digested with KpnI to construct a plasmid carrying dapA and dapB autonomously replicable in coryneform bacteria. The constructed plasmid was designated as pAB. The process of construction of pAB is shown in FIG. 11.

<7> Construction of Plasmid Carrying Mutant lysC, dapA, and dapB Together p399DPS was digested with EcoRI and SphI followed by blunt end formation to extract a dapA gene fragment. This fragment was ligated with the p399AK9 having been digested with SalI and blunt-ended to construct a plasmid p399CA in which mutant lysC and dapA co-existed.

The plasmid pCRDAPB carrying dapB was digested with EcoRI and blunt-ended, followed by digestion with SacI to extract a DNA fragment of 2.0 kb comprising dapB. The plasmid p399CA carrying dapA and mutant lysC was digested with SpeI and blunt-ended, and was thereafter digested with SacI and ligated with the extracted dapB fragment to obtain a plasmid carrying mutant lysC, dapA, and dapB. This plasmid was designated as p399CAB.

Figure 12:
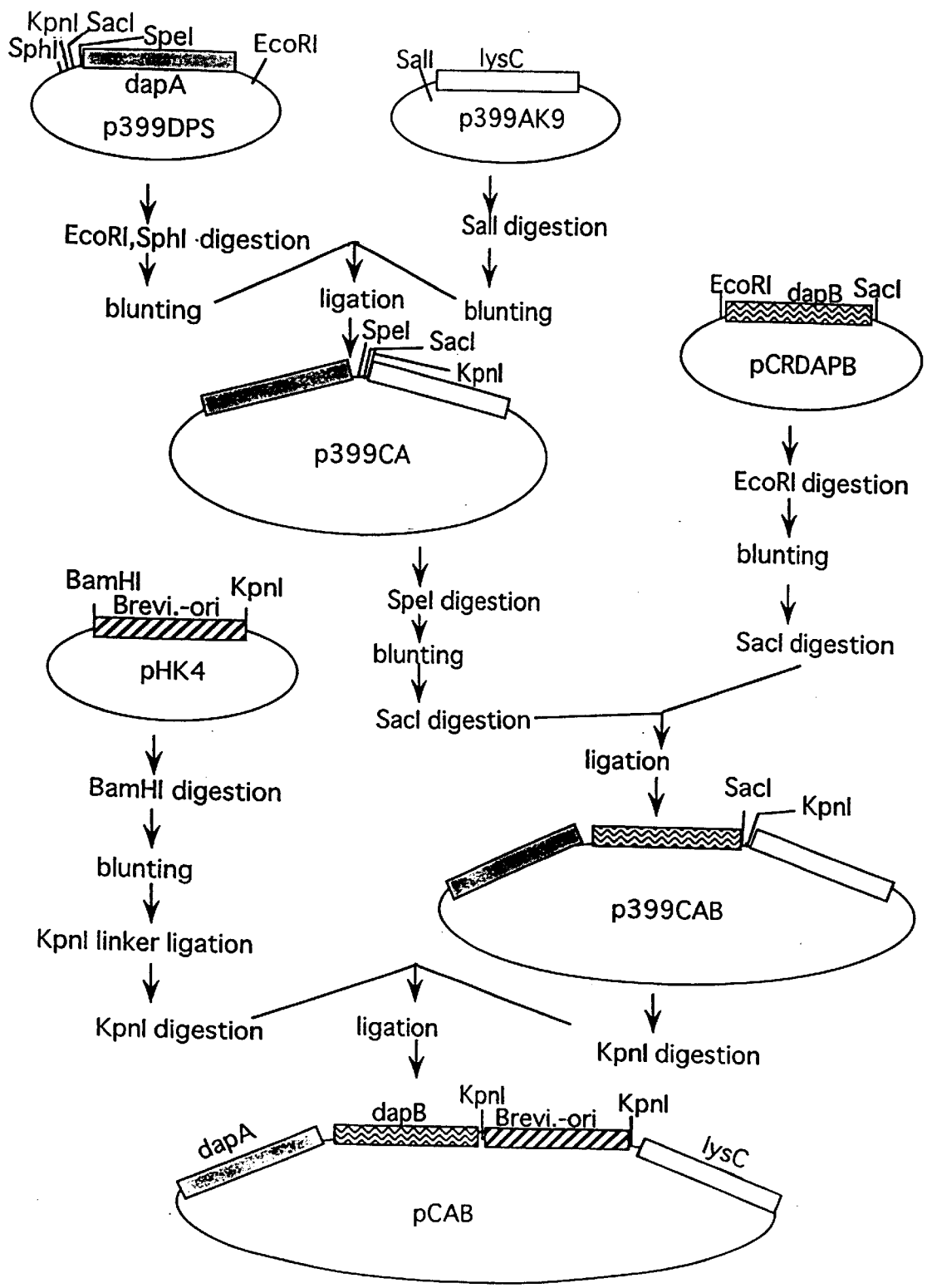
FIG. 12 illustrates a process of construction of a plasmid pCAB carrying mutant lysC, dapA, dapB, and Brevi.-ori.

Next, Brevi.-ori was introduced into p399CAB. The plasmid pHK4 carrying Brevi.-ori was digested with a restriction enzyme BamHI (produced by Takara Shuzo), and cleaved ends were blunted. Blunt end formation was performed by using DNA Blunting kit (produced by Takara Shuzo) in accordance with a designated method. After the blunt end formation, a phosphorylated KpnI linker (produced by Takara Shuzo) was ligated to make modification so that the DNA fragment corresponding to the Brevi.-ori portion might be excised from pHK4 by digestion with only KpnI. This plasmid was digested with KpnI, and the generated Brevi.-ori DNA fragment was ligated with p399CAB having been also digested with KpnI to construct a plasmid carrying mutant lysC, dapA, and dapB together autonomously replicable in coryneform bacteria. The constructed plasmid was designated as pCAB. The process of construction of pCAB is shown in FIG. 12.

<8> Construction of Plasmid Carrying Mutant lysC, dapA, dapB, and lysA Together

Figure 13:
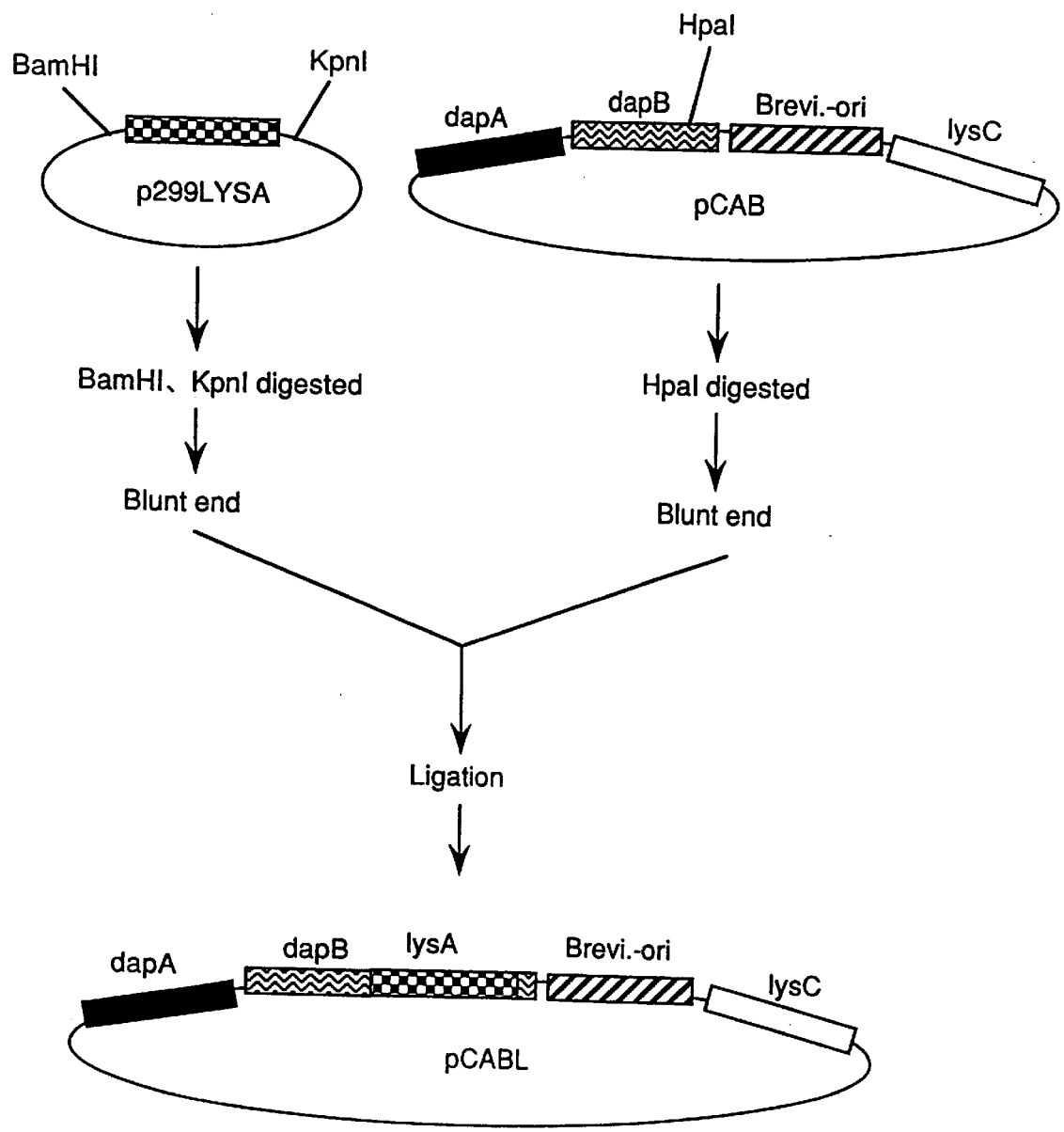
FIG. 13 illustrates a process of construction of a plasmid pCABL carrying mutant lysC, dapA, dapB, lysA, and Brevi.-ori.

The plasmid p299LYSA carrying lysA was digested with KpnI and BamHI and blunt-ended, and then a lysA gene fragment was extracted. This fragment was ligated with pCAB having been digested with HpaI (produced by Takara Shuzo) and blunt-ended to construct a plasmid carrying mutant lysC, dapA, dapB, and lysA together autonomously replicable in coryneform bacteria. The constructed plasmid was designated as pCABL. The process of construction of pCABL is shown in FIG. 13. It is noted that the lysA gene fragment is inserted into a HpaI site in a DNA fragment containing the dapB gene in pCABL, however, the HpaI site is located upstream from a promoter for the dapB gene (nucleotide numbers 611 to 616 in SEQ ID NO: 23), and the dapB gene is not divided.

Figure 14:
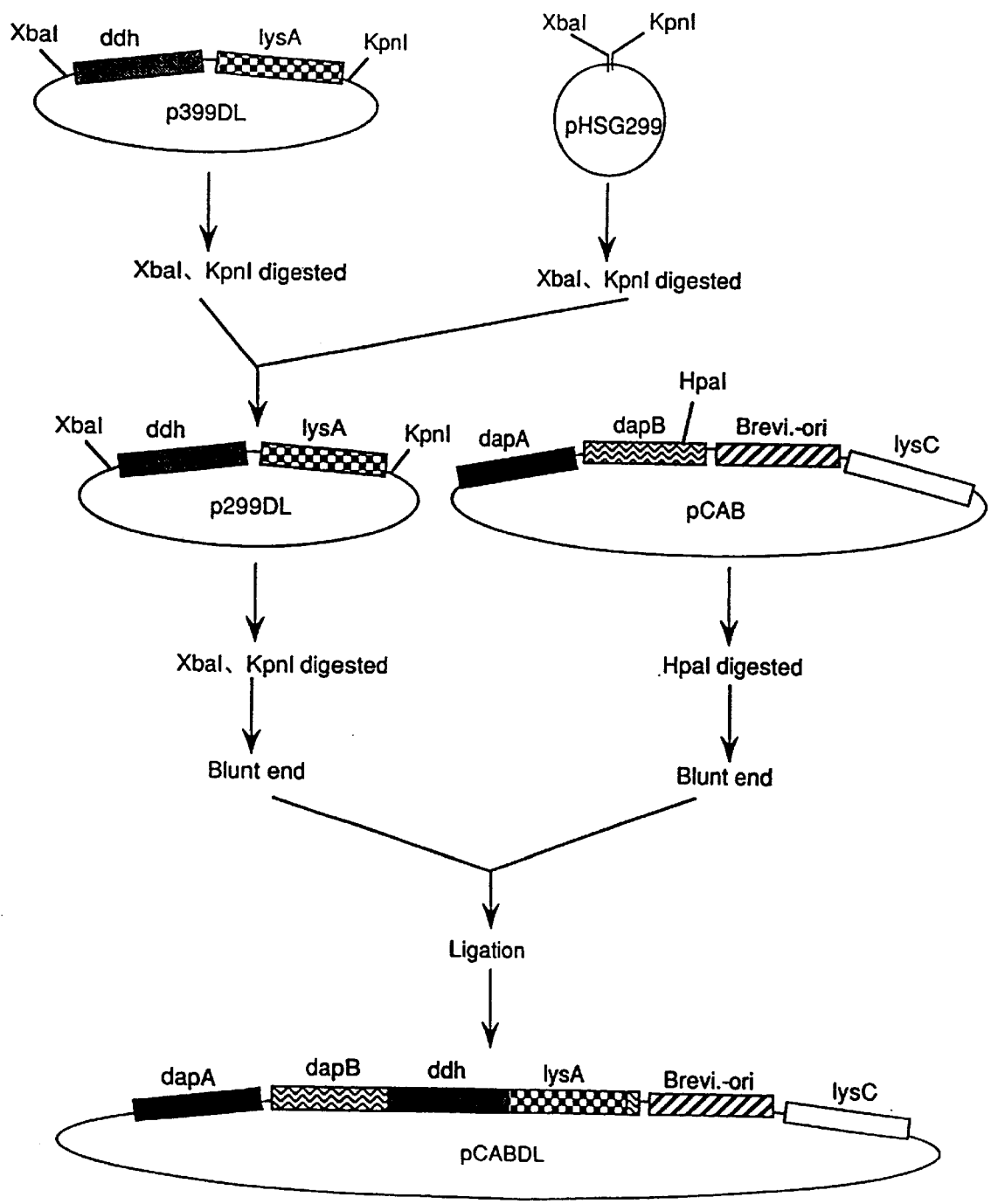
FIG. 14 illustrates a process of construction of a plasmid pCABDL carrying mutant lysC, dapB, ddh, lysA, and Brevi.-ori.

<9> Construction of Plasmid Carrying Mutant lysC, dapA, dapB, ddh, and lysA Together pHSG299 was digested with XbaI and KpnI, and was ligated with p399DL carrying ddh and lysA having been digested with XbaI and KpnI. A constructed plasmid was designated as p299DL. p299DL was digested with XbaI and KpnI and blunt-ended. After the blunt end formation, a DNA fragment carrying ddh and lysA was extracted. This DNA fragment was ligated with the plasmid pCAB carrying mutant lysC, dapA, and dapB together having been digested with HpaI and blunt-ended to construct a plasmid carrying mutant lysC, dapA, dapB, lysA and ddh together autonomously replicable in coryneform bacteria. The constructed plasmid was designated as pCABDL. The process of construction of pCABDL is shown in FIG. 14.

EXAMPLE 5: Introduction of Plasmids Carrying Genes for L-Lysine Biosynthesis into L-Lysine-Producing Bacterium of *Brevibacterium lactofermentum*

The plasmids carrying the genes for L-lysine biosynthesis constructed as described above, namely pLYSAB(Cm″), pPK4D(Cm″), p399AK9B(Cm″), PDPSB(Km″), pDPRB (Cm″), pCRCAB(Km″), pAB(Cm″), pDL(Cm″), pCB(Cm″), pCAB(Cm″), pCABL(Cm″), and pCABDL(Cm″) were introduced into an L-lysine-producing bacterium AJ11082 (NRRL B-11470) of *Brevibacterium lactofermentum* respectively. AJ11082 strain has a property of AEC resistance. The plasmids were introduced in accordance with an electric pulse method (Sugimoto et al., Japanese Patent Application Laid-open No. 2-207791). Transformants were selected based on drug resistance markers possessed by the respective plasmids. Transformants were selected on a complete medium containing 5 µg/ml of chloramphenicol when a plasmid carrying a chloramphenicol resistance gene was introduced, or transformants were selected on a complete medium containing 25 µg/ml of kanamycin when a plasmid carrying a kanamycin resistance gene was introduced.

EXAMPLE 6: Production of L-Lysine

Each of the transformants obtained in Example 5 was cultivated in an L-lysine-producing medium to evaluate its L-lysine productivity. The L-lysine-producing medium had the following composition. [L-Lysine-producing medium]

The following components other than calcium carbonate (per liter) were dissolved to make adjustment at pH 8.0 with KOH. The medium was sterilized at 115° C. for 15 minutes, and calcium carbonate (50 g) having been separately sterilized in hot air in a dry state was added to the sterilized medium.

| | |
|---|---|
| Glucose | 100 g |
| (NH$_4$)$_2$SO$_4$ | 55 g |
| KH$_2$PO$_4$ | 1 g |
| MgSO$_4$ · 7H$_2$O | 1 g |
| Biotin | 500 µg |
| Thiamin | 2000 µg |
| FeSO$_4$ · 7H$_2$O | 0.01 g |
| MnSO$_4$ · 7H$_2$O | 0.01 g |
| Nicotinamide | 5 mg |
| Protein hydrolysate (Mamenou) | 30 ml |
| Calcium carbonate | 50 g |

Each of the various types of the transformants and the parent strain was inoculated to the medium having the composition described above to perform cultivation at 31.5° C. with reciprocating shaking. The amount of produced L-lysine after 40 or 72 hours of cultivation, and the growth after 72 hours (OD$_{562}$) are shown in Table 1. In the table, lysC* represents mutant lysC. The growth was quantitatively determined by measuring OD at 560 nm after 101-fold dilution.

TABLE 1

Accumulation of L-Lysine after Cultivation for 40 or 72 Hours

| Bacterial strain/ plasmid | Introduced gene | Amount of produced L-lysine (g/L) after 40 hrs | after 72 hrs | Growth (OD$_{562}$/ 101) |
|---|---|---|---|---|
| AJ11082 | | 22.0 | 29.8 | 0.450 |
| AJ11082/pLYSAB | lysA | 19.8 | 32.5 | 0.356 |
| AJ11082/pPK4D | ddh | 19.0 | 33.4 | 0.330 |
| AJ11082/p399AK9B | lysC* | 16.8 | 34.5 | 0.398 |
| AJ11082/pDPSB | dapA | 18.7 | 33.8 | 0.410 |
| AJ11082/pDPRB | dapB | 19.9 | 29.9 | 0.445 |
| AJ11082/pCRCAB | lysC*, dapA | 19.7 | 36.5 | 0.360 |
| AJ11082/pAB | dapA, dapB | 19.0 | 34.8 | 0.390 |
| AJ11082/pDL | lysA, ddh | 23.3 | 31.6 | 0.440 |
| AJ11082/pCB | lysC*, dapB | 23.3 | 35.0 | 0.440 |
| AJ11082/pCAB | lysC*, dapA, dapB | 23.0 | 45.0 | 0.425 |
| AJ11082/pCABL | lysC*, dapA, dapB, lysA | 26.2 | 46.5 | 0.379 |
| AJ11082/pCABDL | lysC*, dapA, dapB, lysA, ddh | 26.5 | 47.0 | 0.409 |

As shown above, when lysA, ddh, mutant lysC, dapA, or dapB was enhanced singly, the amount of produced L-lysine after 72 hours of cultivation was larger than or equivalent to that produced by the parent strain, however, the amount of produced L-lysine after 40 hours of cultivation was smaller than that produced by the parent strain. Namely, the L-lysine-producing speed was lowered in cultivation for a short period. Similarly, when mutant lysC and dapA, or dapA and dapB were enhanced in combination, the amount of produced L-lysine after 72 hours of cultivation was larger than that produced by the parent strain, however, the amount of produced L-lysine after 40 hours of cultivation was smaller than that produced by the parent strain. Thus the L-lysine-producing speed was lowered.

On the other hand, when only lysA and ddh were enhanced in combination, the growth was improved, the L-lysine-producing speed was successfully restored in the short period of cultivation, and the accumulated amount of L-lysine was also improved in cultivation for a long period.

Also, in the case of the strain in which dapB was enhanced together with mutant lysC, and in the case of the strain in which dapA as well as these genes were simultaneously enhanced, the growth was improved and the L-lysine-producing speed was increased compared with the parent strain. In the case of the strain in which these three genes were simultaneously enhanced, both of the L-lysine-producing speed and the amount of accumulated L-lysine were further improved by further enhancing lysA and ddh.

What is claimed is:

1. A method for producing L-lysine comprising the steps of cultivating a coryneform bacterium in which a DNA sequence coding for a diaminopimelate decarboxylase, and a DNA sequence coding for a diaminopimelate dehydrogenase are enhanced, in a medium, to allow L-lysine to be produced and accumulated in a culture, and collecting L-lysine from the culture.

2. A method for producing L-lysine comprising the steps of cultivating a coryneform bacterium which is transformed by introduction of a recombinant DNA autonomously replicable in cells of coryneform bacteria said, recombinant DNA comprising a DNA sequence coding for a diaminopimelate decarboxylase, and a DNA sequence coding for a diaminopimelate dehydrogenase, in a medium, to allow L-lysine to be produced and accumulated in a culture, and collecting L-lysine from the culture.

3. The method of claim 2, wherein said coryneform bacterium belongs to the genus Corynebacterium or the genus Brevibacterium.

4. The method of claim 3, wherein said coryneform bacterium belongs to the genus Corynebacterium.

5. The method of claim 3, wherein said coryneform bacterium belongs to the genus Brevibacterium.

6. The method of claim 2, wherein the DNA sequence coding for a diaminopimelate decarboxylase comprises SEQ ID NO.:3.

7. The method of claim 2, wherein the coryneform bacterium which is transformed is AJ11082.

8. The method of claim 2, wherein the transformed coryneform bacterium is AJ11082 which has been transformed with plasmid pDL.

* * * * *

UNITED STATES PATENT AND TRADEMARK OFFICE
CERTIFICATE OF CORRECTION

PATENT NO. : 6,090,597
DATED : July 18, 2000
INVENTOR(S) : Hirano et al.

Page 1 of 1

It is certified that error appears in the above-identified patent and that said Letters Patent is hereby corrected as shown below:

Column 9,
Line 38, "23." should read -- 19. --;
Line 39, "24." should read -- 20. --;
Line 43, "24," should read -- 20, --;

Column 15,
Line 13, "17 and 18" should read -- 21 and 22 --.

Column 63,
Line 45, "bacteria said," should read -- bacteria, said --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc="Synthetic DNA"

(iv) ANTI-SENSE: NO (xi) SEQUENCE DESCRIPTION: SEQ ID NO:1:

```
GTGGAGCCGA CCATTCCGCG AGG                                              23
```

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc="Synthetic DNA"

(iv) ANTI-SENSE: YES (xi) SEQUENCE DESCRIPTION: SEQ ID NO:2:

```
CCAAAACCGC CCTCCACGGC GAA                                              23
```

(2) INFORMATION FOR SEQ ID NO:3:

(i) SEQUENCE CHARACTERISTICS:
        (A) LENGTH: 3579 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 533..2182

(ix) FEATURE:
        (A) NAME/KEY: CDS
        (B) LOCATION: 2188..3522

(xi) SEQUENCE DESCRIPTION: SEQ ID NO:3:

```
GTGGAGCCGA CCATTCCGCG AGGCTGCACT GCAACGAGGT CGTAGTTTTG GTACATGGCT      60
TCTGGCCAGT TCATGGATTG GCTGCCGAAG AAGCTATAGG CATCGCACCA GGGCCACCGA     120
GTTACCGAAG ATGGTGCCGT GCTTTTCGCC TTGGGCAGGG ACCTTGACAA AGCCCACGCT     180
GATATCGCCA AGTGAGGGAT CAGAATAGTG CATGGGCACG TCGATGCTGC ACATTGAGC      240
GGAGGCAATA TCTACCTGAG GTGGGCATTC TTCCCAGCGG ATGTTTTCTT GCGCTGCTGC     300
AGTGGGCATT GATACCAAAA AGGGGCTAAG CGCAGTCGAG GCGGCAAGAA CTGCTACTAC     360
CCTTTTTATT GTCGAACGGG GCATTACGGC TCCAAGGACG TTTGTTTTCT GGGTCAGTTA     420
CCCCAAAAAG CATATACAGA GACCAATGAT TTTTCATTAA AAAGGCAGGG ATTTGTTATA     480
AGTATGGGTC GTATTCTGTG CGACGGGTGT ACCTCGGCTA GAATTTCTCC CC ATG         535
                                                             Met
```

```
                                                        1
ACA CCA GCT GAT CTC GCA ACA TTG ATT AAA GAG ACC GCG GTA GAG GTT        583
Thr Pro Ala Asp Leu Ala Thr Leu Ile Lys Glu Thr Ala Val Glu Val
            5                   10                  15

TTG ACC TCC CGC GAG CTC GAT ACT TCT GTT CTT CCG GAG CAG GTA GTT        631
Leu Thr Ser Arg Glu Leu Asp Thr Ser Val Leu Pro Glu Gln Val Val
        20                  25                  30

GTG GAG CGT CCG CGT AAC CCA GAG CAC GGC GAT TAC GCC ACC AAC ATT        679
Val Glu Arg Pro Arg Asn Pro Glu His Gly Asp Tyr Ala Thr Asn Ile
    35                  40                  45

GCA TTG CAG GTG GCT AAA AAG GTC GGT CAG AAC CCT CGG GAT TTG GCT        727
Ala Leu Gln Val Ala Lys Lys Val Gly Gln Asn Pro Arg Asp Leu Ala
50                  55                  60                  65

ACC TGG CTG GCA GAG GCA TTG GCT GCA GAT GAC GCC ATT GAT TCT GCT        775
Thr Trp Leu Ala Glu Ala Leu Ala Ala Asp Asp Ala Ile Asp Ser Ala
                70                  75                  80

GAA ATT GCT GGC CCA GGC TTT TTG AAC ATT CGC CTT GCA GCA GCA            823
Glu Ile Ala Gly Pro Gly Phe Leu Asn Ile Arg Leu Ala Ala Ala Ala
            85                  90                  95

CAG GGT GAA ATT GTG GCC AAG ATT CTG GCA CAG GGC GAG ACT TTC GGA        871
Gln Gly Glu Ile Val Ala Lys Ile Leu Ala Gln Gly Glu Thr Phe Gly
        100                 105                 110

AAC TCC GAT CAC CTT TCC CAC TTG GAC GTG AAC CTC GAG TTC GTT TCT        919
Asn Ser Asp His Leu Ser His Leu Asp Val Asn Leu Glu Phe Val Ser
    115                 120                 125

GCA AAC CCA ACC GGA CCT ATT CAC CTT GGC GGA ACC CGC TGG GCT GCC        967
Ala Asn Pro Thr Gly Pro Ile His Leu Gly Gly Thr Arg Trp Ala Ala
130                 135                 140                 145

GTG GGT GAC TCT TTG GGT CGT GTG CTG GAG GCT TCC GGC GCG AAA GTG       1015
Val Gly Asp Ser Leu Gly Arg Val Leu Glu Ala Ser Gly Ala Lys Val
                150                 155                 160

ACC CGC GAA TAC TAC TTC AAC GAT CAC GGT CGC CAG ATC GAT CGT TTC       1063
Thr Arg Glu Tyr Tyr Phe Asn Asp His Gly Arg Gln Ile Asp Arg Phe
            165                 170                 175

GCT TTG TCC CTT CTT GCA GCG GCG AAG GGC GAG CCA ACG CCA GAA GAC       1111
Ala Leu Ser Leu Leu Ala Ala Ala Lys Gly Glu Pro Thr Pro Glu Asp
        180                 185                 190

GGT TAT GGC GGC GAA TAC ATT AAG GAA ATT GCG GAG GCA ATC GTC GAA       1159
Gly Tyr Gly Gly Glu Tyr Ile Lys Glu Ile Ala Glu Ala Ile Val Glu
    195                 200                 205

AAG CAT CCT GAA GCG TTG GCT TTG GAG CCT GCC GCA ACC CAG GAG CTT       1207
Lys His Pro Glu Ala Leu Ala Leu Glu Pro Ala Ala Thr Gln Glu Leu
210                 215                 220                 225

TTC CGC GCT GAA GGC GTG GAG ATG ATG TTC GAG CAC ATC AAA TCT TCC       1255
Phe Arg Ala Glu Gly Val Glu Met Met Phe Glu His Ile Lys Ser Ser
                230                 235                 240

CTG CAT GAG TTC GGC ACC GAT TTC GAT GTC TAC TAC CAC GAG AAC TCC       1303
Leu His Glu Phe Gly Thr Asp Phe Asp Val Tyr Tyr His Glu Asn Ser
            245                 250                 255

CTG TTC GAG TCC GGT GCG GTG GAC AAG GCC GTG CAG GTG CTG AAG GAC       1351
Leu Phe Glu Ser Gly Ala Val Asp Lys Ala Val Gln Val Leu Lys Asp
        260                 265                 270

AAC GGC AAC CTG TAC GAA AAC GAG GGC GCT TGG TGG CTG CGT TCC ACC       1399
Asn Gly Asn Leu Tyr Glu Asn Glu Gly Ala Trp Trp Leu Arg Ser Thr
    275                 280                 285

GAA TTC GGC GAT GAC AAA GAC CGC GTG GTG ATC AAG TCT GAC GGC GAC       1447
Glu Phe Gly Asp Asp Lys Asp Arg Val Val Ile Lys Ser Asp Gly Asp
290                 295                 300                 305

GCA GCC TAC ATC GCT GGC GAT ATC GCG TAC GTG GCT GAT AAG TTC TCC       1495
```

```
Ala Ala Tyr Ile Ala Gly Asp Ile Ala Tyr Val Ala Asp Lys Phe Ser
            310                 315                 320

CGC GGA CAC AAC CTA AAC ATC TAC ATG TTG GGT GCT GAC CAC CAT GGT         1543
Arg Gly His Asn Leu Asn Ile Tyr Met Leu Gly Ala Asp His His Gly
            325                 330                 335

TAC ATC GCG CGC CTG AAG GCA GCG GCG GCA CTT GGC TAC AAG CCA             1591
Tyr Ile Ala Arg Leu Lys Ala Ala Ala Ala Leu Gly Tyr Lys Pro
            340                 345                 350

GAA GGC GTT GAA GTC CTG ATT GGC CAG ATG GTG AAC CTG CTT CGC GAC         1639
Glu Gly Val Glu Val Leu Ile Gly Gln Met Val Asn Leu Leu Arg Asp
        355                 360                 365

GGC AAG GCA GTG CGT ATG TCC AAG CGT GCA GGC ACC GTG GTC ACC CTA         1687
Gly Lys Ala Val Arg Met Ser Lys Arg Ala Gly Thr Val Val Thr Leu
370                 375                 380                 385

GAT GAC CTC GTT GAA GCA ATC GGC ATC GAT GCG GCG CGT TAC TCC CTG         1735
Asp Asp Leu Val Glu Ala Ile Gly Ile Asp Ala Ala Arg Tyr Ser Leu
            390                 395                 400

ATC CGT TCC TCC GTG GAT TCT TCC CTG GAT ATC GAT CTC GGC CTG TGG         1783
Ile Arg Ser Ser Val Asp Ser Ser Leu Asp Ile Asp Leu Gly Leu Trp
            405                 410                 415

GAA TCC CAG TCC TCC GAC AAC CCT GTG TAC TAC GTG CAG TAC GGA CAC         1831
Glu Ser Gln Ser Ser Asp Asn Pro Val Tyr Tyr Val Gln Tyr Gly His
            420                 425                 430

GCT CGT CTG TGC TCC ATC GCG CGC AAG GCA GAG ACC TTG GGT GTC ACC         1879
Ala Arg Leu Cys Ser Ile Ala Arg Lys Ala Glu Thr Leu Gly Val Thr
        435                 440                 445

GAG GAA GGC GCA GAC CTA TCT CTA CTG ACC CAC GAC CGC GAA GGC GAT         1927
Glu Glu Gly Ala Asp Leu Ser Leu Leu Thr His Asp Arg Glu Gly Asp
450                 455                 460                 465

CTC ATC CGC ACA CTC GGA GAG TTC CCA GCA GTG GTG AAG GCT GCC GCT         1975
Leu Ile Arg Thr Leu Gly Glu Phe Pro Ala Val Val Lys Ala Ala Ala
            470                 475                 480

GAC CTA CGT GAA CCA CAC CGC ATT GCC CGC TAT GCT GAG GAA TTA GCT         2023
Asp Leu Arg Glu Pro His Arg Ile Ala Arg Tyr Ala Glu Glu Leu Ala
            485                 490                 495

GGA ACT TTC CAC CGC TTC TAC GAT TCC TGC CAC ATC CTT CCA AAG GTT         2071
Gly Thr Phe His Arg Phe Tyr Asp Ser Cys His Ile Leu Pro Lys Val
        500                 505                 510

GAT GAG GAT ACG GCA CCA ATC CAC ACA GCA CGT CTG GCA CTT GCA GCA         2119
Asp Glu Asp Thr Ala Pro Ile His Thr Ala Arg Leu Ala Leu Ala Ala
        515                 520                 525

GCA ACC CGC CAG ACC CTC GCT AAC GCC CTG CAC CTG GTT GGC GTT TCC         2167
Ala Thr Arg Gln Thr Leu Ala Asn Ala Leu His Leu Val Gly Val Ser
530                 535                 540                 545

GCA CCG GAG AAG ATG TAACA ATG GCT ACA GTT GAA AAT TTC AAT GAA           2214
Ala Pro Glu Lys Met       Met Ala Thr Val Glu Asn Phe Asn Glu
            550             1                 5

CTT CCC GCA CAC GTA TGG CCA CGC AAT GCC GTG CGC CAA GAA GAC GGC         2262
Leu Pro Ala His Val Trp Pro Arg Asn Ala Val Arg Gln Glu Asp Gly
 10                 15                  20                  25

GTT GTC ACC GTC GCT GGT GTG CCT CTG CCT GAC CTC GCT GAA GAA TAC         2310
Val Val Thr Val Ala Gly Val Pro Leu Pro Asp Leu Ala Glu Glu Tyr
                30                  35                  40

GGA ACC CCA CTG TTC GTA GTC GAC GAG GAC GAT TTC CGT TCC CGC TGT         2358
Gly Thr Pro Leu Phe Val Val Asp Glu Asp Asp Phe Arg Ser Arg Cys
            45                  50                  55

CGC GAC ATG GCT ACC GCA TTC GGT GGA CCA GGC AAT GTG CAC TAC GCA         2406
Arg Asp Met Ala Thr Ala Phe Gly Gly Pro Gly Asn Val His Tyr Ala
        60                  65                  70
```

```
TCT AAA GCG TTC CTG ACC AAG ACC ATT GCA CGT TGG GTT GAT GAA GAG         2454
Ser Lys Ala Phe Leu Thr Lys Thr Ile Ala Arg Trp Val Asp Glu Glu
     75                  80                  85

GGG CTG GCA CTG GAC ATT GCA TCC ATC AAC GAA CTG GGC ATT GCC CTG         2502
Gly Leu Ala Leu Asp Ile Ala Ser Ile Asn Glu Leu Gly Ile Ala Leu
 90                  95                 100                 105

GCC GCT GGT TTC CCC GCC AGC CGT ATC ACC GCG CAC GGC AAC AAC AAA         2550
Ala Ala Gly Phe Pro Ala Ser Arg Ile Thr Ala His Gly Asn Asn Lys
                110                 115                 120

GGC GTA GAG TTC CTG CGC GCG TTG GTT CAA AAC GGT GTG GGA CAC GTG         2598
Gly Val Glu Phe Leu Arg Ala Leu Val Gln Asn Gly Val Gly His Val
            125                 130                 135

GTG CTG GAC TCC GCA CAG GAA CTA GAA CTG TTG GAT TAC GTT GCC GCT         2646
Val Leu Asp Ser Ala Gln Glu Leu Glu Leu Leu Asp Tyr Val Ala Ala
        140                 145                 150

GGT GAA GGC AAG ATT CAG GAC GTG TTG ATC CGC GTA AAG CCA GGC ATC         2694
Gly Glu Gly Lys Ile Gln Asp Val Leu Ile Arg Val Lys Pro Gly Ile
    155                 160                 165

GAA GCA CAC ACC CAC GAG TTC ATC GCC ACT AGC CAC GAA GAC CAG AAG         2742
Glu Ala His Thr His Glu Phe Ile Ala Thr Ser His Glu Asp Gln Lys
170                 175                 180                 185

TTC GGA TTC TCC CTG GCA TCC GGT TCC GCA TTC GAA GCA GCA AAA GCC         2790
Phe Gly Phe Ser Leu Ala Ser Gly Ser Ala Phe Glu Ala Ala Lys Ala
                190                 195                 200

GCC AAC AAC GCA GAA AAC CTG AAC CTG GTT GGC CTG CAC TGC CAC GTT         2838
Ala Asn Asn Ala Glu Asn Leu Asn Leu Val Gly Leu His Cys His Val
            205                 210                 215

GGT TCC CAG GTG TTC GAC GCC GAA GGC TTC AAG CTG GCA GCA GAA CGC         2886
Gly Ser Gln Val Phe Asp Ala Glu Gly Phe Lys Leu Ala Ala Glu Arg
        220                 225                 230

GTG TTG GGC CTG TAC TCA CAG ATC CAC AGC GAA CTG GGC GTT GCC CTT         2934
Val Leu Gly Leu Tyr Ser Gln Ile His Ser Glu Leu Gly Val Ala Leu
    235                 240                 245

CCT GAA CTG GAT CTC GGT GGC GGA TAC GGC ATT GCC TAT ACC GCA GCT         2982
Pro Glu Leu Asp Leu Gly Gly Gly Tyr Gly Ile Ala Tyr Thr Ala Ala
250                 255                 260                 265

GAA GAA CCA CTC AAC GTC GCA GAA GTT GCC TCC GAC CTG CTC ACC GCA         3030
Glu Glu Pro Leu Asn Val Ala Glu Val Ala Ser Asp Leu Leu Thr Ala
                270                 275                 280

GTC GGA AAA ATG GCA GCG GAA CTA GGC ATC GAC GCA CCA ACC GTG CTT         3078
Val Gly Lys Met Ala Ala Glu Leu Gly Ile Asp Ala Pro Thr Val Leu
            285                 290                 295

GTT GAG CCC GGC CGC GCT ATC GCA GGC CCC TCC ACC GTG ACC ATC TAC         3126
Val Glu Pro Gly Arg Ala Ile Ala Gly Pro Ser Thr Val Thr Ile Tyr
        300                 305                 310

GAA GTC GGC ACC ACC AAA GAC GTC CAC GTA GAC GAC GAC AAA ACC CGC         3174
Glu Val Gly Thr Thr Lys Asp Val His Val Asp Asp Asp Lys Thr Arg
    315                 320                 325

CGT TAC ATC GCC GTG GAC GGA GGC ATG TCC GAC AAC ATC CGC CCA GCA         3222
Arg Tyr Ile Ala Val Asp Gly Gly Met Ser Asp Asn Ile Arg Pro Ala
330                 335                 340                 345

CTC TAC GGC TCC GAA TAC GAC GCC CGC GTA GTA TCC CGC TTC GCC GAA         3270
Leu Tyr Gly Ser Glu Tyr Asp Ala Arg Val Val Ser Arg Phe Ala Glu
                350                 355                 360

GGA GAC CCA GTA AGC ACC CGC ATC GTG GGC TCC CAC TGC GAA TCC GGC         3318
Gly Asp Pro Val Ser Thr Arg Ile Val Gly Ser His Cys Glu Ser Gly
            365                 370                 375

GAT ATC CTG ATC AAC GAT GAA ATC TAC CCA TCT GAC ATC ACC AGC GGC         3366
Asp Ile Leu Ile Asn Asp Glu Ile Tyr Pro Ser Asp Ile Thr Ser Gly
        380                 385                 390
```

```
GAC TTC CTT GCA CTC GCA GCC ACC GGC GCA TAC TGC TAC GCC ATG AGC      3414
Asp Phe Leu Ala Leu Ala Ala Thr Gly Ala Tyr Cys Tyr Ala Met Ser
    395                 400                 405

TCC CGC TAC AAC GCC TTC ACA CGG CCC GCC GTC GTG TCC GTC CGC GCT      3462
Ser Arg Tyr Asn Ala Phe Thr Arg Pro Ala Val Val Ser Val Arg Ala
410                 415                 420                 425

GGC AGC TCC CGC CTC ATG CTG CGC CGC GAA ACG CTC GAC GAC ATC CTC      3510
Gly Ser Ser Arg Leu Met Leu Arg Arg Glu Thr Leu Asp Asp Ile Leu
                    430                 435                 440

TCA CTA GAG GCA TAACGCTTTT CGACGCCTGA CCCCGCCCTT CACCTTCGCC          3562
Ser Leu Glu Ala
            445

GTGGAGGGCG GTTTTGG                                                   3579

(2) INFORMATION FOR SEQ ID NO:4:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:4:

Met Thr Pro Ala Asp Leu Ala Thr Leu Ile Lys Glu Thr Ala Val Glu
 1               5                  10                  15

Val Leu Thr Ser Arg Glu Leu Asp Thr Ser Val Leu Pro Glu Gln Val
            20                  25                  30

Val Val Glu Arg Pro Arg Asn Pro Glu His Gly Asp Tyr Ala Thr Asn
        35                  40                  45

Ile Ala Leu Gln Val Ala Lys Lys Val Gly Gln Asn Pro Arg Asp Leu
    50                  55                  60

Ala Thr Trp Leu Ala Glu Leu Ala Ala Asp Ala Ile Asp Ser
65                  70                  75                  80

Ala Glu Ile Ala Gly Pro Gly Phe Leu Asn Ile Arg Leu Ala Ala Ala
                85                  90                  95

Ala Gln Gly Glu Ile Val Ala Lys Ile Leu Ala Gln Gly Glu Thr Phe
            100                 105                 110

Gly Asn Ser Asp His Leu Ser His Leu Asp Val Asn Leu Glu Phe Val
        115                 120                 125

Ser Ala Asn Pro Thr Gly Pro Ile His Leu Gly Gly Thr Arg Trp Ala
    130                 135                 140

Ala Val Gly Asp Ser Leu Gly Arg Val Leu Glu Ala Ser Gly Ala Lys
145                 150                 155                 160

Val Thr Arg Glu Tyr Tyr Phe Asn Asp His Gly Arg Gln Ile Asp Arg
                165                 170                 175

Phe Ala Leu Ser Leu Leu Ala Ala Lys Gly Glu Pro Thr Pro Glu
            180                 185                 190

Asp Gly Tyr Gly Gly Glu Tyr Ile Lys Glu Ile Ala Glu Ala Ile Val
        195                 200                 205

Glu Lys His Pro Glu Ala Leu Ala Leu Glu Pro Ala Ala Thr Gln Glu
    210                 215                 220

Leu Phe Arg Ala Glu Gly Val Glu Met Met Phe Glu His Ile Lys Ser
225                 230                 235                 240

Ser Leu His Glu Phe Gly Thr Asp Phe Asp Val Tyr Tyr His Glu Asn
                245                 250                 255
```

```
Ser Leu Phe Glu Ser Gly Ala Val Asp Lys Ala Val Gln Val Leu Lys
            260                 265                 270

Asp Asn Gly Asn Leu Tyr Glu Asn Glu Gly Ala Trp Trp Leu Arg Ser
            275                 280                 285

Thr Glu Phe Gly Asp Asp Lys Asp Arg Val Val Ile Lys Ser Asp Gly
            290                 295                 300

Asp Ala Ala Tyr Ile Ala Gly Asp Ile Ala Tyr Val Ala Asp Lys Phe
305                 310                 315                 320

Ser Arg Gly His Asn Leu Asn Ile Tyr Met Leu Gly Ala Asp His His
            325                 330                 335

Gly Tyr Ile Ala Arg Leu Lys Ala Ala Ala Ala Leu Gly Tyr Lys
            340                 345                 350

Pro Glu Gly Val Glu Val Leu Ile Gly Gln Met Val Asn Leu Leu Arg
            355                 360                 365

Asp Gly Lys Ala Val Arg Met Ser Lys Arg Ala Gly Thr Val Val Thr
            370                 375                 380

Leu Asp Asp Leu Val Glu Ala Ile Gly Ile Asp Ala Ala Arg Tyr Ser
385                 390                 395                 400

Leu Ile Arg Ser Ser Val Asp Ser Ser Leu Asp Ile Asp Leu Gly Leu
            405                 410                 415

Trp Glu Ser Gln Ser Ser Asp Asn Pro Val Tyr Tyr Val Gln Tyr Gly
            420                 425                 430

His Ala Arg Leu Cys Ser Ile Ala Arg Lys Ala Glu Thr Leu Gly Val
            435                 440                 445

Thr Glu Glu Gly Ala Asp Leu Ser Leu Leu Thr His Asp Arg Glu Gly
            450                 455                 460

Asp Leu Ile Arg Thr Leu Gly Glu Phe Pro Ala Val Val Lys Ala Ala
465                 470                 475                 480

Ala Asp Leu Arg Glu Pro His Arg Ile Ala Arg Tyr Ala Glu Glu Leu
            485                 490                 495

Ala Gly Thr Phe His Arg Phe Tyr Asp Ser Cys His Ile Leu Pro Lys
            500                 505                 510

Val Asp Glu Asp Thr Ala Pro Ile His Thr Ala Arg Leu Ala Leu Ala
            515                 520                 525

Ala Ala Thr Arg Gln Thr Leu Ala Asn Ala Leu His Leu Val Gly Val
            530                 535                 540

Ser Ala Pro Glu Lys Met
545                 550
```

(2) INFORMATION FOR SEQ ID NO:5:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ala Thr Val Glu Asn Phe Asn Glu Leu Pro Ala His Val Trp Pro
 1               5                  10                  15

Arg Asn Ala Val Arg Gln Glu Asp Gly Val Val Thr Val Ala Gly Val
            20                  25                  30

Pro Leu Pro Asp Leu Ala Glu Glu Tyr Gly Thr Pro Leu Phe Val Val
            35                  40                  45

Asp Glu Asp Asp Phe Arg Ser Arg Cys Arg Asp Met Ala Thr Ala Phe
```

```
                50                  55                  60
Gly Gly Pro Gly Asn Val His Tyr Ala Ser Lys Ala Phe Leu Thr Lys
 65                  70                  75                  80

Thr Ile Ala Arg Trp Val Asp Glu Glu Gly Leu Ala Leu Asp Ile Ala
                 85                  90                  95

Ser Ile Asn Glu Leu Gly Ile Ala Leu Ala Ala Gly Phe Pro Ala Ser
                100                 105                 110

Arg Ile Thr Ala His Gly Asn Asn Lys Gly Val Glu Phe Leu Arg Ala
                115                 120                 125

Leu Val Gln Asn Gly Val Gly His Val Val Leu Asp Ser Ala Gln Glu
            130                 135                 140

Leu Glu Leu Leu Asp Tyr Val Ala Ala Gly Glu Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
                180                 185                 190

Gly Ser Ala Phe Glu Ala Ala Lys Ala Ala Asn Asn Ala Glu Asn Leu
            195                 200                 205

Asn Leu Val Gly Leu His Cys His Val Gly Ser Gln Val Phe Asp Ala
210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Ala Glu Glu Pro Leu Asn Val Ala
                260                 265                 270

Glu Val Ala Ser Asp Leu Leu Thr Ala Val Gly Lys Met Ala Ala Glu
            275                 280                 285

Leu Gly Ile Asp Ala Pro Thr Val Leu Val Glu Pro Gly Arg Ala Ile
290                 295                 300

Ala Gly Pro Ser Thr Val Thr Ile Tyr Glu Val Gly Thr Thr Lys Asp
305                 310                 315                 320

Val His Val Asp Asp Lys Thr Arg Arg Tyr Ile Ala Val Asp Gly
                325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
            355                 360                 365

Ile Val Gly Ser His Cys Glu Ser Gly Asp Ile Leu Ile Asn Asp Glu
            370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
                420                 425                 430

Arg Arg Glu Thr Leu Asp Asp Ile Leu Ser Leu Glu Ala
            435                 440                 445

(2) INFORMATION FOR SEQ ID NO:6:

(i) SEQUENCE CHARACTERISTICS:
        (A) LENGTH: 20 base pairs
```

```
            (B) TYPE: nucleic acid
            (C) STRANDEDNESS: single
            (D) TOPOLOGY: linear (ii) MOLECULE TYPE: other nucleic acid
            (A) DESCRIPTION: /desc="Synthetic DNA"

(iv) ANTI-SENSE: NO (xi) SEQUENCE DESCRIPTION: SEQ ID NO:6:

CATCTAAGTA TGCATCTCGG                                              20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc="Synthetic DNA"

(iv) ANTI-SENSE: YES (xi) SEQUENCE DESCRIPTION: SEQ ID NO:7:

TGCCCCTCGA GCTAAATTAG                                              20

(2) INFORMATION FOR SEQ ID NO:8:

(i) SEQUENCE CHARACTERISTICS:
            (A) LENGTH: 1034 base pairs
            (B) TYPE: nucleic acid
            (C) STRANDEDNESS: double
            (D) TOPOLOGY: linear (ii) MOLECULE TYPE: Genomic DNA (vi) ORIGINAL SOURCE:
            (A) ORGANISM: Brevibacterium lactofermentum
            (B) STRAIN: ATCC 13869

(ix) FEATURE:
            (A) NAME/KEY: CDS
            (B) LOCATION: 61..1020

(xi) SEQUENCE DESCRIPTION: SEQ ID NO:8:

ATGCATCTCG GTAAGCTCGA CCAGGACAGT GCCACCACAA TTTTGGAGGA TTACAAGAAC    60

ATG ACC AAC ATC CGC GTA GCT ATC GTG GGC TAC GGA AAC CTG GGA CGC    108
Met Thr Asn Ile Arg Val Ala Ile Val Gly Tyr Gly Asn Leu Gly Arg
  1               5                  10                  15

AGC GTC GAA AAG CTT ATT GCC AAG CAG CCC GAC ATG GAC CTT GTA GGA    156
Ser Val Glu Lys Leu Ile Ala Lys Gln Pro Asp Met Asp Leu Val Gly
             20                  25                  30

ATC TTC TCG CGC CGG GCC ACC CTC GAC ACA AAG ACG CCA GTC TTT GAT    204
Ile Phe Ser Arg Arg Ala Thr Leu Asp Thr Lys Thr Pro Val Phe Asp
         35                  40                  45

GTC GCC GAC GTG GAC AAG CAC GCC GAC GAC GTG GAC GTG CTG TTC CTG    252
Val Ala Asp Val Asp Lys His Ala Asp Asp Val Asp Val Leu Phe Leu
     50                  55                  60

TGC ATG GGC TCC GCC ACC GAC ATC CCT GAG CAG GCA CCA AAG TTC GCG    300
Cys Met Gly Ser Ala Thr Asp Ile Pro Glu Gln Ala Pro Lys Phe Ala
 65                  70                  75                  80

CAG TTC GCC TGC ACC GTA GAC ACC TAC GAC AAC CAC CGC GAC ATC CCA    348
Gln Phe Ala Cys Thr Val Asp Thr Tyr Asp Asn His Arg Asp Ile Pro
                 85                  90                  95

CGC CAC CGC CAG GTC ATG AAC GAA GCC GCC ACC GCA GCC GGC AAC GTT    396
```

```
Arg His Arg Gln Val Met Asn Glu Ala Ala Thr Ala Ala Gly Asn Val
            100                 105                 110

GCA CTG GTC TCT ACC GGC TGG GAT CCA GGA ATG TTC TCC ATC AAC CGC      444
Ala Leu Val Ser Thr Gly Trp Asp Pro Gly Met Phe Ser Ile Asn Arg
            115                 120                 125

GTC TAC GCA GCG GCA GTC TTA GCC GAG CAC CAG CAG CAC ACC TTC TGG      492
Val Tyr Ala Ala Ala Val Leu Ala Glu His Gln Gln His Thr Phe Trp
            130                 135                 140

GGC CCA GGT TTG TCA CAG GGC CAC TCC GAT GCT TTG CGA CGC ATC CCT      540
Gly Pro Gly Leu Ser Gln Gly His Ser Asp Ala Leu Arg Arg Ile Pro
145                 150                 155                 160

GGC GTT CAA AAG GCA GTC CAG TAC ACC CTC CCA TCC GAA GAC GCC CTG      588
Gly Val Gln Lys Ala Val Gln Tyr Thr Leu Pro Ser Glu Asp Ala Leu
                165                 170                 175

GAA AAG GCC CGC CGC GGC GAA GCC GGC GAC CTT ACC GGA AAG CAA ACC      636
Glu Lys Ala Arg Arg Gly Glu Ala Gly Asp Leu Thr Gly Lys Gln Thr
            180                 185                 190

CAC AAG CGC CAA TGC TTC GTG GTT GCC GAC GCG GCC GAT CAC GAG CGC      684
His Lys Arg Gln Cys Phe Val Val Ala Asp Ala Ala Asp His Glu Arg
            195                 200                 205

ATC GAA AAC GAC ATC CGC ACC ATG CCT GAT TAC TTC GTT GGC TAC GAA      732
Ile Glu Asn Asp Ile Arg Thr Met Pro Asp Tyr Phe Val Gly Tyr Glu
210                 215                 220

GTC GAA GTC AAC TTC ATC GAC GAA GCA ACC TTC GAC TCC GAG CAC ACC      780
Val Glu Val Asn Phe Ile Asp Glu Ala Thr Phe Asp Ser Glu His Thr
225                 230                 235                 240

GGC ATG CCA CAC GGT GGC CAC GTG ATT ACC ACC GGC GAC ACC GGT GGC      828
Gly Met Pro His Gly Gly His Val Ile Thr Thr Gly Asp Thr Gly Gly
                245                 250                 255

TTC AAC CAC ACC GTG GAA TAC ATC CTC AAG CTG GAC CGA AAC CCA GAT      876
Phe Asn His Thr Val Glu Tyr Ile Leu Lys Leu Asp Arg Asn Pro Asp
            260                 265                 270

TTC ACC GCT TCC TCA CAG ATC GCT TTC GGT CGC GCA GCT CAC CGC ATG      924
Phe Thr Ala Ser Ser Gln Ile Ala Phe Gly Arg Ala Ala His Arg Met
            275                 280                 285

AAG CAG CAG GGC CAA AGC GGA GCT TTC ACC GTC CTC GAA GTT GCT CCA      972
Lys Gln Gln Gly Gln Ser Gly Ala Phe Thr Val Leu Glu Val Ala Pro
            290                 295                 300

TAC CTG CTC TCC CCA GAG AAC TTG GAC GAT CTG ATC GCA CGC GAC GTC     1020
Tyr Leu Leu Ser Pro Glu Asn Leu Asp Asp Leu Ile Ala Arg Asp Val
305                 310                 315                 320

TAATTTAGCT CGAG                                                     1034
```

(2) INFORMATION FOR SEQ ID NO:9:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:9:

```
Met Thr Asn Ile Arg Val Ala Ile Val Gly Tyr Gly Asn Leu Gly Arg
1               5                   10                  15

Ser Val Glu Lys Leu Ile Ala Lys Gln Pro Asp Met Asp Leu Val Gly
                20                  25                  30

Ile Phe Ser Arg Arg Ala Thr Leu Asp Thr Lys Thr Pro Val Phe Asp
            35                  40                  45

Val Ala Asp Val Asp Lys His Ala Asp Asp Val Asp Val Leu Phe Leu
```

-continued

```
                50                  55                  60
Cys Met Gly Ser Ala Thr Asp Ile Pro Glu Gln Ala Pro Lys Phe Ala
 65                  70                  75                  80

Gln Phe Ala Cys Thr Val Asp Thr Tyr Asp Asn His Arg Asp Ile Pro
                 85                  90                  95

Arg His Arg Gln Val Met Asn Glu Ala Ala Thr Ala Ala Gly Asn Val
                100                 105                 110

Ala Leu Val Ser Thr Gly Trp Asp Pro Gly Met Phe Ser Ile Asn Arg
                115                 120                 125

Val Tyr Ala Ala Ala Val Leu Ala Glu His Gln Gln His Thr Phe Trp
130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
                165                 170                 175

Glu Lys Ala Arg Arg Gly Glu Ala Gly Asp Leu Thr Gly Lys Gln Thr
                180                 185                 190

His Lys Arg Gln Cys Phe Val Val Ala Asp Ala Ala Asp His Glu Arg
                195                 200                 205

Ile Glu Asn Asp Ile Arg Thr Met Pro Asp Tyr Phe Val Gly Tyr Glu
210                 215                 220

Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
                245                 250                 255

Phe Asn His Thr Val Glu Tyr Ile Leu Lys Leu Asp Arg Asn Pro Asp
                260                 265                 270

Phe Thr Ala Ser Ser Gln Ile Ala Phe Gly Arg Ala Ala His Arg Met
                275                 280                 285

Lys Gln Gln Gly Gln Ser Gly Ala Phe Thr Val Leu Glu Val Ala Pro
290                 295                 300

Tyr Leu Leu Ser Pro Glu Asn Leu Asp Asp Leu Ile Ala Arg Asp Val
305                 310                 315                 320
```

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc="Synthetic DNA"

(iv) ANTI-SENSE: NO (xi) SEQUENCE DESCRIPTION: SEQ ID NO:10:

TCGCGAAGTA GCACCTGTCA CTT                                             23

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc="Synthetic DNA"

(iv) ANTI-SENSE: YES (xi) SEQUENCE DESCRIPTION: SEQ ID NO:11:

ACGGAATTCA ATCTTACGGC C                                                      21

(2) INFORMATION FOR SEQ ID NO:12:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Brevibacterium lactofermentum
        (B) STRAIN: ATCC 13869

(xi) SEQUENCE DESCRIPTION: SEQ ID NO:12:

TCGCGAAGTA GCACCTGTCA CTTTTGTCTC AAATATTAAA TCGAATATCA ATATACGGTC    60

TGTTTATTGG AACGCATCCC AGTGGCTGAG ACGCATCCGC TAAAGCCCCA GGAACCCTGT   120

GCAGAAAGAA AACACTCCTC TGGCTAGGTA GACACAGTTT ATAAAGGTAG AGTTGAGCGG   180

GTAACTGTCA GCACGTAGAT CGAAAGGTGC ACAAGGTGG CCCTGGTCGT ACAGAAATAT    240

GGCGGTTCCT CGCTTGAGAG TGCGGAACGC ATTAGAAACG TCGCTGAACG GATCGTTGCC   300

ACCAAGAAGG CTGGAAATGA TGTCGTGGTT GTCTGCTCCG CAATGGGAGA CACCACGGAT   360

GAACTTCTAG AACTTGCAGC GGCAGTGAAT CCCGTTCCGC CAGCTCGTGA AATGGATATG   420

CTCCTGACTG CTGGTGAGCG TATTTCTAAC GCTCTCGTCG CCATGGCTAT TGAGTCCCTT   480

GGCGCAGAAG CTCAATCTTT CACTGGCTCT CAGGCTGGTG TGCTCACCAC CGAGCGCCAC   540

GGAAACGCAC GCATTGTTGA CGTCACACCG GGTCGTGTGG GTGAAGCACT CGATGAGGGC   600

AAGATCTGCA TTGTTGCTGG TTTTCAGGGT GTTAATAAAG AAACCCGCGA TGTCACCACG   660

TTGGGTCGTG GTGGTTCTGA CACCACTGCA GTTGCGTTGG CAGCTGCTTT GAACGCTGAT   720

GTGTGTGAGA TTTACTCGGA CGTTGACGGT GTGTATACCG CTGACCCGCG CATCGTTCCT   780

AATGCACAGA AGCTGGAAAA GCTCAGCTTC GAAGAAATGC TGGAACTTGC TGCTGTTGGC   840

TCCAAGATTT TGGTGCTGCG CAGTGTTGAA TACGCTCGTG CATTCAATGT GCCACTTCGC   900

GTACGCTCGT CTTATAGTAA TGATCCCGGC ACTTTGATTG CCGGCTCTAT GGAGGATATT   960

CCTGTGGAAG AAGCAGTCCT TACCGGTGTC GCAACCGACA AGTCCGAAGC CAAAGTAACC  1020

GTTCTGGGTA TTTCCGATAA GCCAGGCGAG GCTGCCAAGG TTTTCCGTGC GTTGGCTGAT  1080

GCAGAAATCA ACATTGACAT GGTTCTGCAG AACGTCTCCT CTGTGGAAGA CGGCACCACC  1140

GACATCACGT TCACCTGCCC TCGCGCTGAC GGACGCCGTG CGATGGAGAT CTTGAAGAAG  1200

CTTCAGGTTC AGGGCAACTG GACCAATGTG CTTTACGACG ACCAGGTCGG CAAAGTCTCC  1260

CTCGTGGGTG CTGGCATGAA GTCTCACCCA GGTGTTACCG CAGAGTTCAT GGAAGCTCTG  1320

CGCGATGTCA ACGTGAACAT CGAATTGATT TCCACCTCTG AGATCCGCAT TTCCGTGCTG  1380

ATCCGTGAAG ATGATCTGGA TGCTGCTGCA CGTGCATTGC ATGAGCAGTT CCAGCTGGGC  1440

GGCGAAGACG AAGCCGTCGT TTATGCAGGC ACCGGACGCT AAAGTTTTAA AGGAGTAGTT  1500

TTACAATGAC CACCATCGCA GTTGTTGGTG CAACCGGCCA GGTCGGCCAG GTTATGCGCA  1560

CCCTTTTGGA AGAGCGCAAT TTCCCAGCTG ACACTGTTCG TTTCTTTGCT TCCCCGCGTT  1620

CCGCAGGCCG TAAGATTGAA TTC                                         1643

(2) INFORMATION FOR SEQ ID NO:13:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 217..1482

(xi) SEQUENCE DESCRIPTION: SEQ ID NO:13:

```
TCGCGAAGTA GCACCTGTCA CTTTTGTCTC AAATATTAAA TCGAATATCA ATATACGGTC      60

TGTTTATTGG AACGCATCCC AGTGGCTGAG ACGCATCCGC TAAAGCCCCA GGAACCCTGT     120

GCAGAAAGAA AACACTCCTC TGGCTAGGTA GACACAGTTT ATAAAGGTAG AGTTGAGCGG     180

GTAACTGTCA GCACGTAGAT CGAAAGGTGC ACAAAG GTG GCC CTG GTC GTA CAG      234
                                    Met Ala Leu Val Val Gln
                                     1               5

AAA TAT GGC GGT TCC TCG CTT GAG AGT GCG GAA CGC ATT AGA AAC GTC      282
Lys Tyr Gly Gly Ser Ser Leu Glu Ser Ala Glu Arg Ile Arg Asn Val
         10              15                  20

GCT GAA CGG ATC GTT GCC ACC AAG AAG GCT GGA AAT GAT GTC GTG GTT      330
Ala Glu Arg Ile Val Ala Thr Lys Lys Ala Gly Asn Asp Val Val Val
         25                  30                  35

GTC TGC TCC GCA ATG GGA GAC ACC ACG GAT GAA CTT CTA GAA CTT GCA      378
Val Cys Ser Ala Met Gly Asp Thr Thr Asp Glu Leu Leu Glu Leu Ala
 40                  45                  50

GCG GCA GTG AAT CCC GTT CCG CCA GCT CGT GAA ATG GAT ATG CTC CTG      426
Ala Ala Val Asn Pro Val Pro Pro Ala Arg Glu Met Asp Met Leu Leu
 55                  60                  65                  70

ACT GCT GGT GAG CGT ATT TCT AAC GCT CTC GTC GCC ATG GCT ATT GAG      474
Thr Ala Gly Glu Arg Ile Ser Asn Ala Leu Val Ala Met Ala Ile Glu
                 75                  80                  85

TCC CTT GGC GCA GAA GCT CAA TCT TTC ACT GGC TCT CAG GCT GGT GTG      522
Ser Leu Gly Ala Glu Ala Gln Ser Phe Thr Gly Ser Gln Ala Gly Val
                 90                  95                 100

CTC ACC ACC GAG CGC CAC GGA AAC GCA CGC ATT GTT GAC GTC ACA CCG      570
Leu Thr Thr Glu Arg His Gly Asn Ala Arg Ile Val Asp Val Thr Pro
                105                 110                 115

GGT CGT GTG CGT GAA GCA CTC GAT GAG GGC AAG ATC TGC ATT GTT GCT      618
Gly Arg Val Arg Glu Ala Leu Asp Glu Gly Lys Ile Cys Ile Val Ala
        120                 125                 130

GGT TTT CAG GGT GTT AAT AAA GAA ACC CGC GAT GTC ACC ACG TTG GGT      666
Gly Phe Gln Gly Val Asn Lys Glu Thr Arg Asp Val Thr Thr Leu Gly
135                 140                 145                 150

CGT GGT GGT TCT GAC ACC ACT GCA GTT GCG TTG GCA GCT GCT TTG AAC      714
Arg Gly Gly Ser Asp Thr Thr Ala Val Ala Leu Ala Ala Ala Leu Asn
                155                 160                 165

GCT GAT GTG TGT GAG ATT TAC TCG GAC GTT GAC GGT GTG TAT ACC GCT      762
Ala Asp Val Cys Glu Ile Tyr Ser Asp Val Asp Gly Val Tyr Thr Ala
                170                 175                 180

GAC CCG CGC ATC GTT CCT AAT GCA CAG AAG CTG GAA AAG CTC AGC TTC      810
Asp Pro Arg Ile Val Pro Asn Ala Gln Lys Leu Glu Lys Leu Ser Phe
                185                 190                 195
```

```
GAA GAA ATG CTG GAA CTT GCT GCT GTT GGC TCC AAG ATT TTG GTG CTG      858
Glu Glu Met Leu Glu Leu Ala Ala Val Gly Ser Lys Ile Leu Val Leu
        200                 205                 210

CGC AGT GTT GAA TAC GCT CGT GCA TTC AAT GTG CCA CTT CGC GTA CGC      906
Arg Ser Val Glu Tyr Ala Arg Ala Phe Asn Val Pro Leu Arg Val Arg
215                 220                 225                 230

TCG TCT TAT AGT AAT GAT CCC GGC ACT TTG ATT GCC GGC TCT ATG GAG      954
Ser Ser Tyr Ser Asn Asp Pro Gly Thr Leu Ile Ala Gly Ser Met Glu
                    235                 240                 245

GAT ATT CCT GTG GAA GAA GCA GTC CTT ACC GGT GTC GCA ACC GAC AAG     1002
Asp Ile Pro Val Glu Glu Ala Val Leu Thr Gly Val Ala Thr Asp Lys
                250                 255                 260

TCC GAA GCC AAA GTA ACC GTT CTG GGT ATT TCC GAT AAG CCA GGC GAG     1050
Ser Glu Ala Lys Val Thr Val Leu Gly Ile Ser Asp Lys Pro Gly Glu
            265                 270                 275

GCT GCC AAG GTT TTC CGT GCG TTG GCT GAT GCA GAA ATC AAC ATT GAC     1098
Ala Ala Lys Val Phe Arg Ala Leu Ala Asp Ala Glu Ile Asn Ile Asp
        280                 285                 290

ATG GTT CTG CAG AAC GTC TCC TCT GTG GAA GAC GGC ACC ACC GAC ATC     1146
Met Val Leu Gln Asn Val Ser Ser Val Glu Asp Gly Thr Thr Asp Ile
295                 300                 305                 310

ACG TTC ACC TGC CCT CGC GCT GAC GGA CGC CGT GCG ATG GAG ATC TTG     1194
Thr Phe Thr Cys Pro Arg Ala Asp Gly Arg Arg Ala Met Glu Ile Leu
                315                 320                 325

AAG AAG CTT CAG GTT CAG GGC AAC TGG ACC AAT GTG CTT TAC GAC GAC     1242
Lys Lys Leu Gln Val Gln Gly Asn Trp Thr Asn Val Leu Tyr Asp Asp
                    330                 335                 340

CAG GTC GGC AAA GTC TCC CTC GTG GGT GCT GGC ATG AAG TCT CAC CCA     1290
Gln Val Gly Lys Val Ser Leu Val Gly Ala Gly Met Lys Ser His Pro
                345                 350                 355

GGT GTT ACC GCA GAG TTC ATG GAA GCT CTG CGC GAT GTC AAC GTG AAC     1338
Gly Val Thr Ala Glu Phe Met Glu Ala Leu Arg Asp Val Asn Val Asn
            360                 365                 370

ATC GAA TTG ATT TCC ACC TCT GAG ATC CGC ATT TCC GTG CTG ATC CGT     1386
Ile Glu Leu Ile Ser Thr Ser Glu Ile Arg Ile Ser Val Leu Ile Arg
375                 380                 385                 390

GAA GAT GAT CTG GAT GCT GCT GCA CGT GCA TTG CAT GAG CAG TTC CAG     1434
Glu Asp Asp Leu Asp Ala Ala Ala Arg Ala Leu His Glu Gln Phe Gln
                395                 400                 405

CTG GGC GGC GAA GAC GAA GCC GTC GTT TAT GCA GGC ACC GGA CGC TAA     1482
Leu Gly Gly Glu Asp Glu Ala Val Val Tyr Ala Gly Thr Gly Arg
                410                 415                 420

AGTTTTAAAG GAGTAGTTTT ACAATGACCA CCATCGCAGT TGTTGGTGCA ACCGGCCAGG   1542

TCGGCCAGGT TATGCGCACC CTTTTGGAAG AGCGCAATTT CCCAGCTGAC ACTGTTCGTT   1602

TCTTTGCTTC CCCGCGTTCC GCAGGCCGTA AGATTGAATT C                      1643

(2) INFORMATION FOR SEQ ID NO:14:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO:14:

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
```

-continued

```
                    20                  25                  30
Gly Asn Asp Val Val Val Cys Ser Ala Met Gly Asp Thr Thr Asp
            35                  40                  45
Glu Leu Leu Glu Leu Ala Ala Val Asn Pro Val Pro Pro Ala Arg
     50                  55                  60
Glu Met Asp Met Leu Leu Thr Ala Gly Glu Arg Ile Ser Asn Ala Leu
 65                  70                  75                  80
Val Ala Met Ala Ile Glu Ser Leu Gly Ala Glu Ala Gln Ser Phe Thr
                 85                  90                  95
Gly Ser Gln Ala Gly Val Leu Thr Thr Glu Arg His Gly Asn Ala Arg
                100                 105                 110
Ile Val Asp Val Thr Pro Gly Arg Val Arg Glu Ala Leu Asp Glu Gly
             115                 120                 125
Lys Ile Cys Ile Val Ala Gly Phe Gln Gly Val Asn Lys Glu Thr Arg
             130                 135                 140
Asp Val Thr Thr Leu Gly Arg Gly Gly Ser Asp Thr Thr Ala Val Ala
145                 150                 155                 160
Leu Ala Ala Ala Leu Asn Ala Asp Val Cys Glu Ile Tyr Ser Asp Val
                 165                 170                 175
Asp Gly Val Tyr Thr Ala Asp Pro Arg Ile Val Pro Asn Ala Gln Lys
             180                 185                 190
Leu Glu Lys Leu Ser Phe Glu Glu Met Leu Glu Leu Ala Ala Val Gly
             195                 200                 205
Ser Lys Ile Leu Val Leu Arg Ser Val Glu Tyr Ala Arg Ala Phe Asn
     210                 215                 220
Val Pro Leu Arg Val Arg Ser Ser Tyr Ser Asn Asp Pro Gly Thr Leu
225                 230                 235                 240
Ile Ala Gly Ser Met Glu Asp Ile Pro Val Glu Glu Ala Val Leu Thr
                 245                 250                 255
Gly Val Ala Thr Asp Lys Ser Glu Ala Lys Val Thr Val Leu Gly Ile
             260                 265                 270
Ser Asp Lys Pro Gly Glu Ala Ala Lys Val Phe Arg Ala Leu Ala Asp
     275                 280                 285
Ala Glu Ile Asn Ile Asp Met Val Leu Gln Asn Val Ser Ser Val Glu
 290                 295                 300
Asp Gly Thr Thr Asp Ile Thr Phe Thr Cys Pro Arg Ala Asp Gly Arg
305                 310                 315                 320
Arg Ala Met Glu Ile Leu Lys Lys Leu Gln Val Gln Gly Asn Trp Thr
                 325                 330                 335
Asn Val Leu Tyr Asp Asp Gln Val Gly Lys Val Ser Leu Val Gly Ala
             340                 345                 350
Gly Met Lys Ser His Pro Gly Val Thr Ala Glu Phe Met Glu Ala Leu
     355                 360                 365
Arg Asp Val Asn Val Asn Ile Glu Leu Ile Ser Thr Ser Glu Ile Arg
 370                 375                 380
Ile Ser Val Leu Ile Arg Glu Asp Asp Leu Asp Ala Ala Ala Arg Ala
385                 390                 395                 400
Leu His Glu Gln Phe Gln Leu Gly Gly Glu Asp Glu Ala Val Val Tyr
                 405                 410                 415
Ala Gly Thr Gly Arg
             420
```

(2) INFORMATION FOR SEQ ID NO:15:

(i) SEQUENCE CHARACTERISTICS:
    (A) LENGTH: 1643 base pairs
    (B) TYPE: nucleic acid
    (C) STRANDEDNESS: double
    (D) TOPOLOGY: linear (ii) MOLECULE TYPE: Genomic DNA (vi) ORIGINAL SOURCE:
    (A) ORGANISM: Brevibacterium lactofermentum
    (B) STRAIN: ATCC 13869

(ix) FEATURE:
    (A) NAME/KEY: CDS
    (B) LOCATION: 964..1482

(xi) SEQUENCE DESCRIPTION: SEQ ID NO:15:

```
TCGCGAAGTA GCACCTGTCA CTTTTGTCTC AAATATTAAA TCGAATATCA ATATACGGTC      60

TGTTTATTGG AACGCATCCC AGTGGCTGAG ACGCATCCGC TAAAGCCCCA GGAACCCTGT     120

GCAGAAAGAA AACACTCCTC TGGCTAGGTA GACACAGTTT ATAAAGGTAG AGTTGAGCGG     180

GTAACTGTCA GCACGTAGAT CGAAAGGTGC ACAAAGGTGG CCCTGGTCGT ACAGAAATAT     240

GGCGGTTCCT CGCTTGAGAG TGCGGAACGC ATTAGAAACG TCGCTGAACG GATCGTTGCC     300

ACCAAGAAGG CTGGAAATGA TGTCGTGGTT GTCTGCTCCG CAATGGGAGA CACCACGGAT     360

GAACTTCTAG AACTTGCAGC GGCAGTGAAT CCCGTTCCGC CAGCTCGTGA AATGGATATG     420

CTCCTGACTG CTGGTGAGCG TATTTCTAAC GCTCTCGTCG CCATGGCTAT TGAGTCCCTT     480

GGCGCAGAAG CTCAATCTTT CACTGGCTCT CAGGCTGGTG TGCTCACCAC CGAGCGCCAC     540

GGAAACGCAC GCATTGTTGA CGTCACACCG GGTCGTGTGC GTGAAGCACT CGATGAGGGC     600

AAGATCTGCA TTGTTGCTGG TTTTCAGGGT GTTAATAAAG AAACCCGCGA TGTCACCACG     660

TTGGGTCGTG GTGGTTCTGA CACCACTGCA GTTGCGTTGG CAGCTGCTTT GAACGCTGAT     720

GTGTGTGAGA TTTACTCGGA CGTTGACGGT GTGTATACCG CTGACCCGCG CATCGTTCCT     780

AATGCACAGA AGCTGGAAAA GCTCAGCTTC GAAGAAATGC TGGAACTTGC TGCTGTTGGC     840

TCCAAGATTT TGGTGCTGCG CAGTGTTGAA TACGCTCGTG CATTCAATGT GCCACTTCGC     900

GTACGCTCGT CTTATAGTAA TGATCCCGGC ACTTTGATTG CCGGCTCTAT GGAGGATATT     960

CCT GTG GAA GAA GCA GTC CTT ACC GGT GTC GCA ACC GAC AAG TCC GAA    1008
    Met Glu Glu Ala Val Leu Thr Gly Val Ala Thr Asp Lys Ser Glu
    1               5                  10                  15

GCC AAA GTA ACC GTT CTG GGT ATT TCC GAT AAG CCA GGC GAG GCT GCC    1056
Ala Lys Val Thr Val Leu Gly Ile Ser Asp Lys Pro Gly Glu Ala Ala
                20                  25                  30

AAG GTT TTC CGT GCG TTG GCT GAT GCA GAA ATC AAC ATT GAC ATG GTT    1104
Lys Val Phe Arg Ala Leu Ala Asp Ala Glu Ile Asn Ile Asp Met Val
            35                  40                  45

CTG CAG AAC GTC TCC TCT GTG GAA GAC GGC ACC ACC GAC ATC ACG TTC    1152
Leu Gln Asn Val Ser Ser Val Glu Asp Gly Thr Thr Asp Ile Thr Phe
        50                  55                  60

ACC TGC CCT CGC GCT GAC GGA CGC CGT GCG ATG GAG ATC TTG AAG AAG    1200
Thr Cys Pro Arg Ala Asp Gly Arg Arg Ala Met Glu Ile Leu Lys Lys
    65                  70                  75

CTT CAG GTT CAG GGC AAC TGG ACC AAT GTG CTT TAC GAC GAC CAG GTC    1248
Leu Gln Val Gln Gly Asn Trp Thr Asn Val Leu Tyr Asp Asp Gln Val
80                  85                  90                  95

GGC AAA GTC TCC CTC GTG GGT GCT GGC ATG AAG TCT CAC CCA GGT GTT    1296
Gly Lys Val Ser Leu Val Gly Ala Gly Met Lys Ser His Pro Gly Val
                100                 105                 110
```

-continued

```
ACC GCA GAG TTC ATG GAA GCT CTG CGC GAT GTC AAC GTG AAC ATC GAA      1344
Thr Ala Glu Phe Met Glu Ala Leu Arg Asp Val Asn Val Asn Ile Glu
            115                 120                 125

TTG ATT TCC ACC TCT GAG ATC CGC ATT TCC GTG CTG ATC CGT GAA GAT      1392
Leu Ile Ser Thr Ser Glu Ile Arg Ile Ser Val Leu Ile Arg Glu Asp
            130                 135                 140

GAT CTG GAT GCT GCT GCA CGT GCA TTG CAT GAG CAG TTC CAG CTG GGC      1440
Asp Leu Asp Ala Ala Ala Arg Ala Leu His Glu Gln Phe Gln Leu Gly
    145                 150                 155

GGC GAA GAC GAA GCC GTC GTT TAT GCA GGC ACC GGA CGC TAAAGTTTTAA      1490
Gly Glu Asp Glu Ala Val Val Tyr Ala Gly Thr Gly Arg
160                 165                 170

AGGAGTAGTT TTACAATGAC CACCATCGCA GTTGTTGGTG CAACCGGCCA GGTCGGCCAG    1550

GTTATGCGCA CCCTTTTGGA AGAGCGCAAT TCCCAGCTG ACACTGTTCG TTTCTTTGCT     1610

TCCCCGCGTT CCGCAGGCCG TAAGATTGAA TTC                                 1643
```

(2) INFORMATION FOR SEQ ID NO:16:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO:16:

```
Met Glu Glu Ala Val Leu Thr Gly Val Ala Thr Asp Lys Ser Glu Ala
 1               5                  10                  15

Lys Val Thr Val Leu Gly Ile Ser Asp Lys Pro Gly Glu Ala Ala Lys
            20                  25                  30

Val Phe Arg Ala Leu Ala Asp Ala Glu Ile Asn Ile Asp Met Val Leu
        35                  40                  45

Gln Asn Val Ser Ser Val Glu Asp Gly Thr Thr Asp Ile Thr Phe Thr
    50                  55                  60

Cys Pro Arg Ala Asp Gly Arg Arg Ala Met Glu Ile Leu Lys Lys Leu
65                  70                  75                  80

Gln Val Gln Gly Asn Trp Thr Asn Val Leu Tyr Asp Asp Gln Val Gly
                85                  90                  95

Lys Val Ser Leu Val Gly Ala Gly Met Lys Ser His Pro Gly Val Thr
            100                 105                 110

Ala Glu Phe Met Glu Ala Leu Arg Asp Val Asn Val Asn Ile Glu Leu
        115                 120                 125

Ile Ser Thr Ser Glu Ile Arg Ile Ser Val Leu Ile Arg Glu Asp Asp
    130                 135                 140

Leu Asp Ala Ala Ala Arg Ala Leu His Glu Gln Phe Gln Leu Gly Gly
145                 150                 155                 160

Glu Asp Glu Ala Val Val Tyr Ala Gly Thr Gly Arg
                165                 170
```

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc="Synthetic DNA"

-continued (iv) ANTI-SENSE: NO (xi) SEQUENCE DESCRIPTION: SEQ ID NO:17:

GTCGACGGAT CGCAAATGGC AAC                                              23

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc="Synthetic DNA"

(iv) ANTI-SENSE: YES (xi) SEQUENCE DESCRIPTION: SEQ ID NO:18:

GGATCCTTGA GCACCTTGCG CAG                                              23

(2) INFORMATION FOR SEQ ID NO:19:

(i) SEQUENCE CHARACTERISTICS:
        (A) LENGTH: 1411 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 311..1213

(xi) SEQUENCE DESCRIPTION: SEQ ID NO:19:

```
CTCTCGATAT CGAGAGAGAA GCAGCGCCAC GGTTTTTCGG TGATTTTGAG ATTGAAACTT     60

TGGCAGACGG ATCGCAAATG CAACAAGCC CGTATGTCAT GGACTTTTAA CGCAAAGCTC    120

ACACCCACGA GCTAAAAATT CATATAGTTA AGACAACATT TTTGGCTGTA AAAGACAGCC    180

GTAAAAACCT CTTGCTCATG TCAATTGTTC TTATCGGAAT GTGGCTTGGG CGATTGTTAT    240

GCAAAGTTG TTAGGTTTTT TGCGGGGTTG TTTAACCCCC AAATGAGGGA AGAAGGTAAC    300

CTTGAACTCT ATG AGC ACA GGT TTA ACA GCT AAG ACC GGA GTA GAG CAC       349
           Met Ser Thr Gly Leu Thr Ala Lys Thr Gly Val Glu His
             1               5                  10

TTC GGC ACC GTT GGA GTA GCA ATG GTT ACT CCA TTC ACG GAA TCC GGA       397
Phe Gly Thr Val Gly Val Ala Met Val Thr Pro Phe Thr Glu Ser Gly
 15                  20                  25

GAC ATC GAT ATC GCT GCT GGC CGC GAA GTC GCG GCT TAT TTG GTT GAT       445
Asp Ile Asp Ile Ala Ala Gly Arg Glu Val Ala Ala Tyr Leu Val Asp
 30                  35                  40                  45

AAG GGC TTG GAT TCT TTG GTT CTC GCG GGC ACC ACT GGT GAA TCC CCA       493
Lys Gly Leu Asp Ser Leu Val Leu Ala Gly Thr Thr Gly Glu Ser Pro
                 50                  55                  60

ACG ACA ACC GCC GCT GAA AAA CTA GAA CTG CTC AAG GCC GTT CGT GAG       541
Thr Thr Thr Ala Ala Glu Lys Leu Glu Leu Leu Lys Ala Val Arg Glu
                 65                  70                  75

GAA GTT GGG GAT CGG GCG AAC GTC ATC GCC GGT GTC GGA ACC AAC AAC       589
Glu Val Gly Asp Arg Ala Asn Val Ile Ala Gly Val Gly Thr Asn Asn
                 80                  85                  90
```

```
ACG CGG ACA TCT GTG GAA CTT GCG GAA GCT GCT GCT TCT GCT GGC GCA      637
Thr Arg Thr Ser Val Glu Leu Ala Glu Ala Ala Ala Ser Ala Gly Ala
        95                  100                 105

GAC GGC CTT TTA GTT GTA ACT CCT TAT TAC TCC AAG CCG AGC CAA GAG      685
Asp Gly Leu Leu Val Val Thr Pro Tyr Tyr Ser Lys Pro Ser Gln Glu
110                 115                 120                 125

GGA TTG CTG GCG CAC TTC GGT GCA ATT GCT GCA GCA ACA GAG GTT CCA      733
Gly Leu Leu Ala His Phe Gly Ala Ile Ala Ala Ala Thr Glu Val Pro
                130                 135                 140

ATT TGT CTC TAT GAC ATT CCT GGT CGG TCA GGT ATT CCA ATT GAG TCT      781
Ile Cys Leu Tyr Asp Ile Pro Gly Arg Ser Gly Ile Pro Ile Glu Ser
            145                 150                 155

GAT ACC ATG AGA CGC CTG AGT GAA TTA CCT ACG ATT TTG GCG GTC AAG      829
Asp Thr Met Arg Arg Leu Ser Glu Leu Pro Thr Ile Leu Ala Val Lys
        160                 165                 170

GAC GCC AAG GGT GAC CTC GTT GCA GCC ACG TCA TTG ATC AAA GAA ACG      877
Asp Ala Lys Gly Asp Leu Val Ala Ala Thr Ser Leu Ile Lys Glu Thr
175                 180                 185

GGA CTT GCC TGG TAT TCA GGC GAT GAC CCA CTA AAC CTT GTT TGG CTT      925
Gly Leu Ala Trp Tyr Ser Gly Asp Asp Pro Leu Asn Leu Val Trp Leu
190                 195                 200                 205

GCT TTG GGC GGA TCA GGT TTC ATT TCC GTA ATT GGA CAT GCA GCC CCC      973
Ala Leu Gly Gly Ser Gly Phe Ile Ser Val Ile Gly His Ala Ala Pro
                210                 215                 220

ACA GCA TTA CGT GAG TTG TAC ACA AGC TTC GAG GAA GGC GAC CTC GTC     1021
Thr Ala Leu Arg Glu Leu Tyr Thr Ser Phe Glu Glu Gly Asp Leu Val
            225                 230                 235

CGT GCG CGG GAA ATC AAC GCC AAA CTA TCA CCG CTG GTA GCT GCC CAA     1069
Arg Ala Arg Glu Ile Asn Ala Lys Leu Ser Pro Leu Val Ala Ala Gln
        240                 245                 250

GGT CGC TTG GGT GGA GTC AGC TTG GCA AAA GCT GCT CTG CGT CTG CAG     1117
Gly Arg Leu Gly Gly Val Ser Leu Ala Lys Ala Ala Leu Arg Leu Gln
255                 260                 265

GGC ATC AAC GTA GGA GAT CCT CGA CTT CCA ATT ATG GCT CCA AAT GAG     1165
Gly Ile Asn Val Gly Asp Pro Arg Leu Pro Ile Met Ala Pro Asn Glu
270                 275                 280                 285

CAG GAA CTT GAG GCT CTC CGA GAA GAC ATG AAA AAA GCT GGA GTT CTA     1213
Gln Glu Leu Glu Ala Leu Arg Glu Asp Met Lys Lys Ala Gly Val Leu
                290                 295                 300

TAAATATGAA TGATTCCCGA AATCGCGGCC GGAAGGTTAC CCGCAAGGCG GCCCACCAGA   1273

AGCTGGTCAG GAAAACCATC TGGATACCCC TGTCTTTCAG GCACCAGATG CTTCCTCTAA   1333

CCAGAGCGCT GTAAAAGCTG AGACCGCCGG AAACGACAAT CGGGATGCTG CGCAAGGTGC   1393

TCAAGGATCC CAACATTC                                                1411
```

(2) INFORMATION FOR SEQ ID NO:20:

(i) SEQUENCE CHARACTERISTICS:
        (A) LENGTH: 301 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ser Thr Gly Leu Thr Ala Lys Thr Gly Val Glu His Phe Gly Thr
  1               5                  10                  15

Val Gly Val Ala Met Val Thr Pro Phe Thr Glu Ser Gly Asp Ile Asp
                 20                  25                  30

Ile Ala Ala Gly Arg Glu Val Ala Ala Tyr Leu Val Asp Lys Gly Leu
```

|                    |                    |                    |
|        35          |        40          |        45          |

Asp Ser Leu Val Leu Ala Gly Thr Thr Gly Glu Ser Pro Thr Thr Thr
        50                      55                      60

Ala Ala Glu Lys Leu Glu Leu Leu Lys Ala Val Arg Glu Glu Val Gly
 65                      70                      75                      80

Asp Arg Ala Asn Val Ile Ala Gly Val Gly Thr Asn Asn Thr Arg Thr
                85                      90                      95

Ser Val Glu Leu Ala Glu Ala Ala Ser Ala Gly Ala Asp Gly Leu
            100                     105                     110

Leu Val Val Thr Pro Tyr Tyr Ser Lys Pro Ser Gln Glu Gly Leu Leu
            115                     120                     125

Ala His Phe Gly Ala Ile Ala Ala Thr Glu Val Pro Ile Cys Leu
        130                     135                     140

Tyr Asp Ile Pro Gly Arg Ser Gly Ile Pro Ile Glu Ser Asp Thr Met
145                     150                     155                     160

Arg Arg Leu Ser Glu Leu Pro Thr Ile Leu Ala Val Lys Asp Ala Lys
            165                     170                     175

Gly Asp Leu Val Ala Ala Thr Ser Leu Ile Lys Glu Thr Gly Leu Ala
            180                     185                     190

Trp Tyr Ser Gly Asp Asp Pro Leu Asn Leu Val Trp Leu Ala Leu Gly
        195                     200                     205

Gly Ser Gly Phe Ile Ser Val Ile Gly His Ala Ala Pro Thr Ala Leu
    210                     215                     220

Arg Glu Leu Tyr Thr Ser Phe Glu Glu Gly Asp Leu Val Arg Ala Arg
225                     230                     235                     240

Glu Ile Asn Ala Lys Leu Ser Pro Leu Val Ala Ala Gln Gly Arg Leu
                245                     250                     255

Gly Gly Val Ser Leu Ala Lys Ala Ala Leu Arg Leu Gln Gly Ile Asn
            260                     265                     270

Val Gly Asp Pro Arg Leu Pro Ile Met Ala Pro Asn Glu Gln Glu Leu
        275                     280                     285

Glu Ala Leu Arg Glu Asp Met Lys Lys Ala Gly Val Leu
        290                     295                     300

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc="Synthetic DNA"

(iv) ANTI-SENSE: NO (xi) SEQUENCE DESCRIPTION: SEQ ID NO:21:

GGATCCCCAA TCGATACCTG GAA                                                    23

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc="Synthetic DNA"

(iv) ANTI-SENSE: YES (xi) SEQUENCE DESCRIPTION: SEQ ID NO:22:

CGGTTCATCG CCAAGTTTTT CTT                                                        23

(2) INFORMATION FOR SEQ ID NO:23:

(i) SEQUENCE CHARACTERISTICS:
        (A) LENGTH: 2001 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Brevibacterium lactofermentum
        (B) STRAIN: ATCC 13869

(ix) FEATURE:
        (A) NAME/KEY: CDS
        (B) LOCATION: 730..1473

(xi) SEQUENCE DESCRIPTION: SEQ ID NO:23:

```
GGATCCCCAA TCGATACCTG AACGACAAC CTGATCAGGA TATCCAATGC CTTGAATATT      60

GACGTTGAGG AAGGAATCAC CAGCCATCTC AACTGGAAGA CCTGACGCCT GCTGAATTGG    120

ATCAGTGGCC CAATCGACCC ACCAACCAGG TTGGCTATTA CCGGCGATAT CAAAAACAAC    180

TCGCGTGAAC GTTTCGTGCT CGGCAACGCG GATGCCAGCG ATCGACATAT CGGAGTCACC    240

AACTTGAGCC TGCTGCTTCT GATCCATCGA CGGGGAACCC AACGGCGGCA AGCAGTGGG     300

GGAAGGGGAG TTGGTGGACT CTGAATCAGT GGGCTCTGAA GTGGTAGGCG ACGGGCAGC     360

ATCTGAAGGC GTGCGAGTTG TGGTGACCGG GTTAGCGGTT TCAGTTTCTG TCACAACTGG    420

AGCAGGACTA GCAGAGGTTG TAGGCGTTGA GCCGCTTCCA TCACAAGCAC TTAAAAGTAA    480

AGAGGCGGAA ACCACAAGCG CCAAGGAACT ACCTGCGGAA CGGGCGGTGA AGGGCAACTT    540

AAGTCTCATA TTTCAAACAT AGTTCCACCT GTGTGATTAA TCTCCAGAAC GGAACAAACT    600

GATGAACAAT CGTTAACAAC ACAGACCAAA ACGGTCAGTT AGGTATGGAT ATCAGCACCT    660

TCTGAATGGG TACGTCTAGA CTGGTGGGCG TTTGAAAAAC TCTTCGCCCC ACGAAAATGA    720
```

```
AGGAGCATA ATG GGA ATC AAG GTT GGC GTT CTC GGA GCC AAA GGC CGT              768
           Met Gly Ile Lys Val Gly Val Leu Gly Ala Lys Gly Arg
             1               5                  10

GTT GGT CAA ACT ATT GTG GCA GCA GTC AAT GAG TCC GAC GAT CTG GAG            816
Val Gly Gln Thr Ile Val Ala Ala Val Asn Glu Ser Asp Asp Leu Glu
 15                  20                  25

CTT GTT GCA GAG ATC GGC GTC GAC GAT GAT TTG AGC CTT CTG GTA GAC            864
Leu Val Ala Glu Ile Gly Val Asp Asp Asp Leu Ser Leu Leu Val Asp
 30                  35                  40                  45

AAC GGC GCT GAA GTT GTC GTT GAC TTC ACC ACT CCT AAC GCT GTG ATG            912
Asn Gly Ala Glu Val Val Val Asp Phe Thr Thr Pro Asn Ala Val Met
             50                  55                  60

GGC AAC CTG GAG TTC TGC ATC AAC AAC GGC ATT TCT GCG GTT GTT GGA            960
Gly Asn Leu Glu Phe Cys Ile Asn Asn Gly Ile Ser Ala Val Val Gly
             65                  70                  75

ACC ACG GGC TTC GAT GAT GCT CGT TTG GAG CAG GTT CGC GCC TGG CTT           1008
Thr Thr Gly Phe Asp Asp Ala Arg Leu Glu Gln Val Arg Ala Trp Leu
             80                  85                  90

GAA GGA AAA GAC AAT GTC GGT GTT CTG ATC GCA CCT AAC TTT GCT ATC           1056
Glu Gly Lys Asp Asn Val Gly Val Leu Ile Ala Pro Asn Phe Ala Ile
             95                  100                 105
```

```
TCT GCG GTG TTG ACC ATG GTC TTT TCC AAG CAG GCT GCC CGC TTC TTC    1104
Ser Ala Val Leu Thr Met Val Phe Ser Lys Gln Ala Ala Arg Phe Phe
110                 115                 120                 125

GAA TCA GCT GAA GTT ATT GAG CTG CAC CAC CCC AAC AAG CTG GAT GCA    1152
Glu Ser Ala Glu Val Ile Glu Leu His His Pro Asn Lys Leu Asp Ala
                130                 135                 140

CCT TCA GGC ACC GCG ATC CAC ACT GCT CAG GGC ATT GCT GCG GCA CGC    1200
Pro Ser Gly Thr Ala Ile His Thr Ala Gln Gly Ile Ala Ala Ala Arg
            145                 150                 155

AAA GAA GCA GGC ATG GAC GCA CAG CCA GAT GCG ACC GAG CAG GCA CTT    1248
Lys Glu Ala Gly Met Asp Ala Gln Pro Asp Ala Thr Glu Gln Ala Leu
        160                 165                 170

GAG GGT TCC CGT GGC GCA AGC GTA GAT GGA ATC CCA GTT CAC GCA GTC    1296
Glu Gly Ser Arg Gly Ala Ser Val Asp Gly Ile Pro Val His Ala Val
175                 180                 185

CGC ATG TCC GGC ATG GTT GCT CAC GAG CAA GTT ATC TTT GGC ACC CAG    1344
Arg Met Ser Gly Met Val Ala His Glu Gln Val Ile Phe Gly Thr Gln
190                 195                 200                 205

GGT CAG ACC TTG ACC ATC AAG CAG GAC TCC TAT GAT CGC AAC TCA TTT    1392
Gly Gln Thr Leu Thr Ile Lys Gln Asp Ser Tyr Asp Arg Asn Ser Phe
                210                 215                 220

GCA CCA GGT GTC TTG GTG GGT GTG CGC AAC ATT GCA CAG CAC CCA GGC    1440
Ala Pro Gly Val Leu Val Gly Val Arg Asn Ile Ala Gln His Pro Gly
            225                 230                 235

CTA GTC GTA GGA CTT GAG CAT TAC CTA GGC CTG TAAAGGCTCA TTTCAGCAGC  1493
Leu Val Val Gly Leu Glu His Tyr Leu Gly Leu
        240                 245

GGGTGGAATT TTTTAAAAGG AGCGTTTAAA GGCTGTGGCC GAACAAGTTA AATTGAGCGT  1553

GGAGTTGATA GCGTGCAGTT CTTTTACTCC ACCCGCTGAT GTTGAGTGGT CAACTGATGT  1613

TGAGGGCGCG GAAGCACTCG TCGAGTTTGC GGGTCGTGCC TGCTACGAAA CTTTTGATAA  1673

GCCGAACCCT CGAACTGCTT CCAATGCTGC GTATCTGCGC ACACATCATGG AAGTGGGGCA  1733

CACTGCTTTG CTTGAGCATG CCAATGCCAC GATGTATATC CGAGGCATTT CTCGGTCCGC  1793

GACCCATGAA TTGGTCCGAC ACCGCCATTT TTCCTTCTCT CAACTGTCTC AGCGTTTCGT  1853

GCACAGCGGA GAATCGGAAG TAGTGGTGCC CACTCTCATC GATGAAGATC CGCAGTTGCG  1913

TGAACTTTTC ATGCACGCCA TGGATGAGTC TCGGTTCGCT TTCAATGAGC TGCTTAATGC  1973

GCTGGAAGAA AAACTTGGCG ATGAACCG                                     2001

(2) INFORMATION FOR SEQ ID NO:24:

(i) SEQUENCE CHARACTERISTICS:
        (A) LENGTH: 248 amino acids
        (B) TYPE: amino acid
        (D) TOPOLOGY: linear (ii) MOLECULE TYPE: protein (xi) SEQUENCE DESCRIPTION: SEQ ID NO:24:

Met Gly Ile Lys Val Gly Val Leu Gly Ala Lys Gly Arg Val Gly Gln
 1               5                  10                  15

Thr Ile Val Ala Ala Val Asn Glu Ser Asp Asp Leu Glu Leu Val Ala
                20                  25                  30

Glu Ile Gly Val Asp Asp Leu Ser Leu Leu Val Asp Asn Gly Ala
            35                  40                  45

Glu Val Val Val Asp Phe Thr Thr Pro Asn Ala Val Met Gly Asn Leu
        50                  55                  60
```

-continued

```
Glu Phe Cys Ile Asn Asn Gly Ile Ser Ala Val Val Gly Thr Thr Gly
 65                  70                  75                  80

Phe Asp Asp Ala Arg Leu Glu Gln Val Arg Ala Trp Leu Glu Gly Lys
                 85                  90                  95

Asp Asn Val Gly Val Leu Ile Ala Pro Asn Phe Ala Ile Ser Ala Val
            100                 105                 110

Leu Thr Met Val Phe Ser Lys Gln Ala Ala Arg Phe Phe Glu Ser Ala
        115                 120                 125

Glu Val Ile Glu Leu His His Pro Asn Lys Leu Asp Ala Pro Ser Gly
    130                 135                 140

Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245
```